(12) United States Patent
Raredon et al.

(10) Patent No.: US 9,986,734 B2
(45) Date of Patent: Jun. 5, 2018

(54) HUMAN AND LARGE-MAMMAL LUNG BIOREACTOR

(71) Applicants: YALE UNIVERSITY, New Haven, CT (US); RAREDON RESOURCES, INC., Northampton, MA (US)

(72) Inventors: Micha Sam Brickman Raredon, Somerville, MA (US); Tom Raredon, Northampton, MA (US); Laura Niklason, New Haven, CT (US)

(73) Assignees: Yale University, New Haven, CT (US); Raredon Resources, Inc., Northampton, MA (US)

( * ) Notice: Subject to any disclaimer, the term of this patent is extended or adjusted under 35 U.S.C. 154(b) by 178 days.

(21) Appl. No.: 14/749,889

(22) Filed: Jun. 25, 2015

(65) Prior Publication Data

US 2015/0289501 A1    Oct. 15, 2015

Related U.S. Application Data

(63) Continuation of application No. PCT/US2014/010688, filed on Jan. 8, 2014.
(Continued)

(51) Int. Cl.
*A01N 1/02* (2006.01)
*A61K 35/42* (2015.01)
(Continued)

(52) U.S. Cl.
CPC ............ *A01N 1/0263* (2013.01); *A61K 35/42* (2013.01); *A61L 27/3804* (2013.01);
(Continued)

(58) Field of Classification Search
CPC ....................................... A01N 1/0236–1/0247
See application file for complete search history.

(56) References Cited

U.S. PATENT DOCUMENTS 3,717,199 A * 2/1973 Dienst ..................... F28F 23/00
165/46
5,356,771 A * 10/1994 O'Dell ..................... A01N 1/02
261/122.1
(Continued)

FOREIGN PATENT DOCUMENTS

JP   2012-516699 A   2/2010
JP   2012-528600 A   11/2012
(Continued)

OTHER PUBLICATIONS

Bijonowski, et al., "Bioreactor design for perfusion-based, highly-vascularized organ regeneration", Curr. Opin. Chem. Eng.: 2(1), 2012, 32-40.
(Continued)

*Primary Examiner* — William H. Beisner
(74) *Attorney, Agent, or Firm* — Saul Ewing Arnstein & Lehr LLP; Kathryn Doyle; Brian R. Landry

(57) ABSTRACT

The present invention provides a bioreactor for large-mammal lung tissue. The bioreactor is capable of hydraulic driven negative-pressure and positive-pressure perfusion and ventilation. Perfusion and ventilation is delivered at physiological rates and is easily controllable. In one embodiment, the bioreactor comprises a support scaffold to support the size of a large-mammal lung tissue. In another embodiment, the bioreactor comprises a pleural sack that provides a small isolated fluid chamber which surrounds an engineered lung, thereby minimizing the amount of culture media needed. The present invention also provides an in vitro model for examining the function of a test agent and compositions and methods for alleviating a lung defect in a large-mammal.

23 Claims, 10 Drawing Sheets

Related U.S. Application Data

(60) Provisional application No. 61/750,088, filed on Jan. 8, 2013.

(51) Int. Cl.

| | |
|---|---|
| *C12M 3/00* | (2006.01) |
| *C12M 1/00* | (2006.01) |
| *C12M 1/12* | (2006.01) |
| *C12M 1/34* | (2006.01) |
| *C12M 1/36* | (2006.01) |
| *A61L 27/38* | (2006.01) |
| *G01N 33/50* | (2006.01) |
| *C12N 5/071* | (2010.01) |

(52) U.S. Cl.
CPC ....... *A61L 27/3839* (2013.01); *A61L 27/3895* (2013.01); *C12M 21/08* (2013.01); *C12M 23/00* (2013.01); *C12M 23/50* (2013.01); *C12M 23/52* (2013.01); *C12M 25/14* (2013.01); *C12M 29/10* (2013.01); *C12M 41/46* (2013.01); *C12M 41/48* (2013.01); *C12N 5/0688* (2013.01); *G01N 33/5088* (2013.01); *A61L 2430/40* (2013.01); *C12N 2533/90* (2013.01)

(56) References Cited

U.S. PATENT DOCUMENTS

| | | | | |
|---|---|---|---|---|
| 5,807,737 | A | * | 9/1998 | Schill ........... A01N 1/02 435/1.2 |
| 2008/0017194 | A1 | * | 1/2008 | Hassanein ........ A01N 1/02 128/200.24 |
| 2012/0064050 | A1 | | 3/2012 | Calle et al. |
| 2012/0141439 | A1 | | 7/2012 | Ott |
| 2013/0323708 | A1 | | 12/2013 | Yarmush et al. |

FOREIGN PATENT DOCUMENTS

| | | |
|---|---|---|
| WO | 2010091188 A1 | 8/2010 |
| WO | 2010128464 A1 | 11/2010 |
| WO | 2010141803 A2 | 12/2010 |

OTHER PUBLICATIONS

Petersen, "Bioreactor for the Long-Term Culture of Lung Tissue", Cell Transplant: 20(7), 2011, 1117-26.
European Search Report for European Patent Application No. 14738132.1 dated Aug. 19, 2016.
Nichols et al,. "Engineering of a Complex Organ—Progress Toward Development of a Tissue-engineered Lung", 2008, Proc. Am. Thor. Soc. 5:723-30.
Satchell et al., "Angiopoietin 1 and Vascular Endothelial Growth Factor Modulate Human Glomerular Endothelial Cell Barrier Properties", 2004, J. Am. Soc. Nephrol. 15:566-74.
Atala et al., "Tissue-engineered autologous bladders for patients needing cystoplaty", 2006, Lancet 367:1241-6.
Orfanos et al., "Pulmonary endothelium in acute lung injury: from basic science to the critically ill", 2004, Intensive Care Med. 30:1702-14.
Calle et al., "Procedure for lung engineering", Mar. 8, 2011, J. Vis. Exp. 49.
Nichols et al., "Production and Utilization of Acellular Lung Scaffolds in Tissue Engineering", Jul. 2012, J. Cell. Biochem. 113:2185-2192.
International Search Report and Written Opinion, International Application No. PCT/US14/10688, dated Mar. 5, 2014.
International Preliminary Report on Patentability, International Application No. PCT/US14/10688, dated Jul. 14, 2015.
Notification of Reasons for Rejection, Japanese Patent Application No. 2015-551859, dated Oct. 26, 2017.
Badylak, et al., "Whole-organ tissue engineering: decellularization and recellularization of three-dimensional matrix scaffolds", Annu Rev Biomed Eng. 13, 2011, 27-53.
Ott, et al., "Regeneration and orthotopic transplantation of a bioartificial lung", Nat Med. 16(8), 2010, 927-933.
Price, et al., "Development of a decellularized lung bioreactor system for bioengineering the lung: the matrix reloaded", Tissue Eng Part A. 16(8), 2010, 2581-2591.
Examination Report No. 1 for Standard Patent Application, Australian Patent Application No. 2014205510, dated Sep. 11, 2017.
Aigner, C., et al., "Clinical Ex Vivo Lung Perfusion—Pushing the Limits", American Journal of Transplantation 2012; 12: 1839-1847.
Cypel, M., et al., "Normothermic Ex Vivo Perfusion Prevents Lung Injury Compared to Extended Cold Preservation for Transplantation", American Journal of Transplantation 2009; 9: 2262-2269.
Cypel, M., et al., "Normothermic Ex Vivo Lung Perfusion in Clinical Lung Transplantation", N Engl J Med 2011;364:1431-40.
Erasmus, M. E., et al., "Normothermic ex vivo lung perfusion of non-heart-beating donor lungs in pigs: from pretransplant function analysis towards a 6-h machine preservation", European Society for Organ Transplantation 19 (2006) 589-593.
Ingemansson, R., et al., "Clinical Transplantation of Initially Rejected Donor Lungs After Reconditioning Ex Vivo", Ann Thorac Surg 2009;87:255-60.
Lindstedt, S., et al., "A Short Period of Ventilation without Perfusion Seems to Reduce Atelectasis without Harming the Lungs during Ex Vivo Lung Perfusion", Journal of Transplantation vol. 2013, Article ID 729286, 6 pages.
Steen, S., et al., "Transplantation of Lungs From Non-Heart-Beating Donors After Functional Assessment Ex Vivo", Ann Thorac Surg 2003;76:244-52.

\* cited by examiner

HUMAN AND LARGE-MAMMAL LUNG BIOREACTOR

CROSS-REFERENCE TO RELATED APPLICATION

This application a continuation under 35 U.S.C. § 120 of International Application No. PCT/US2014/010688, filed Jan. 8, 2014, which claims priority to U.S. Provisional Patent Application Ser. No. 61/750,088, filed Jan. 8, 2013. The entire contents of each of these applications are hereby incorporated herein by reference.

STATEMENT REGARDING FEDERALLY SPONSORED RESEARCH OR DEVELOPMENT

This invention was made with government support under grant number HL111016 awarded by the National Institutes of Health (NIH). The government has certain rights in the invention.

BACKGROUND OF THE INVENTION

Tissue engineering is a growing field that seeks to combine cellular, molecular, technological and medical advances to create replacement tissues suitable for implantation and laboratory study. Promising work has been done on a variety of tissues, including blood vessels, urinary bladder, heart valves, and cardiac tissue (Nichols et al, 2008, Proc Am Thor Soc 5:723-30; Satchell et al., 2004, J Am Soc Nephrol 15:566-74; Atala et al., 2006, Lancet 367:1241-6; Orfanos et al., 2004, Intensive Care Med 30:1702-14). However, lung is a difficult tissue to engineer in the laboratory. Lung requires a complex matrix that can withstand the mechanical pressures of breathing, that can support the growth of endothelial, epithelial and mesenchymal cells, and that provides a means for gas exchange between two very different yet intimately juxtaposed compartments. Further, the engineering of a large-mammal lung, including a human lung, is hampered by the large size of the organ. Difficulties in the effective culture of a human-scale lung include providing an adequate sterile environment and providing structural support of a large and unwieldy organ. Further, the costs of providing culture media to such a large tissue can be preventative.

Thus, there is a need in the art for the development of a bioreactor system for the culture of large-mammal lung tissue. The present invention satisfies this need in the art.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
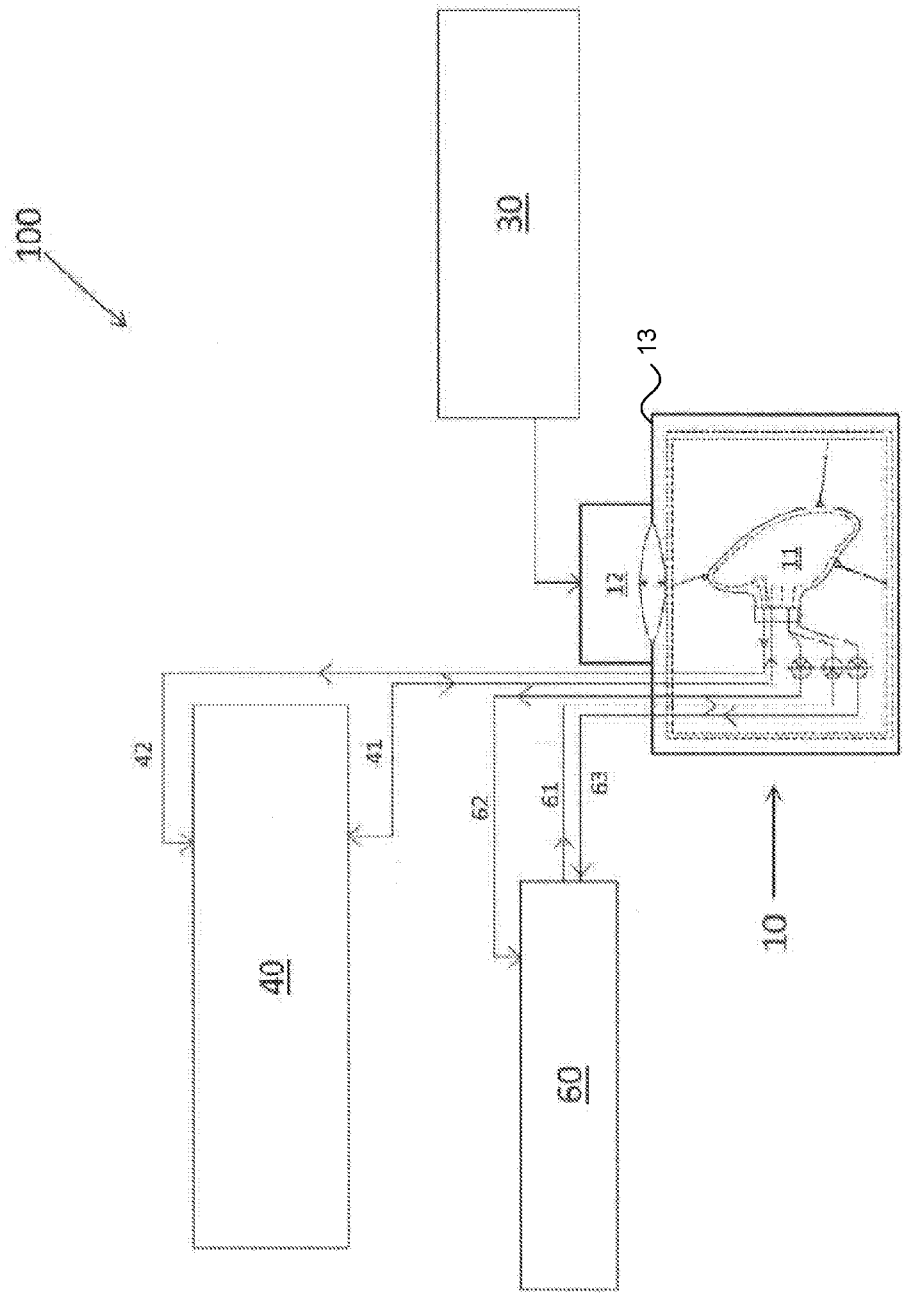
FIG. 1 is a schematic for an exemplary bioreactor system of the invention.

The present invention includes a bioreactor system for the culture of large-mammal lung tissue. In one embodiment, the bioreactor system provides a sterile environment for the decellularization, recellularization, and culture of an engineered human lung. In one embodiment, the bioreactor system provides highly controllable perfusion and ventilation of the engineered lung. In one embodiment, the bioreactor is capable of ventilating and perfusing lungs with various fluids and gases via hydraulically driven negative pressure as well as providing vascular perfusion and ventilation at physiologic rates and pressures. The bioreactor enables among other things the perfusion of fluid through the vasculature, the movement of fluid or air in and out of the airways, and the ventilation of the lungs via negative (as well as positive) pressure.

In one embodiment, the present invention includes an engineered large-mammal lung, cultured in the bioreactor system of the present invention. Accordingly, the invention includes methods and compositions for the generation of vascularized pulmonary tissues as a form of regenerative medicine. In one embodiment, the engineered lung tissue is derived from a decellularized native lung tissue. The decellularized tissues are substantially devoid of cells and DNA. Preferably, the decellularized tissue is also devoid of immunogenic molecules. More preferably, the decellularized tissue retains several key extracellular matrix molecules that are important for cell attachment and proliferation.

In one embodiment, the engineered large-mammal lung includes an in vitro three dimensional model, that for example is useful for investigating lung developmental biology. In addition, the model is useful for among other things, drug discovery, toxicity testing, disease pathology, and the like. In one embodiment, the in vitro model recapitulates the formation of structures reminiscent of alveolar forming units comprised of ductal epithelium tightly interfaced with the host circulation.

The invention also includes a method of alleviating or treating a lung defect in a mammal, preferably a human. The method comprises administering to the mammal in need thereof a therapeutically effective amount of a composition comprising a three dimensional construct of the invention, thereby alleviating or treating the lung defect in the mammal.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in literature often denoted as human embryonic stem (hES) cells, (see, e.g., Thomson et al. (1998), Heins et. al. (2004), as well as induced pluripotent stem cells (see, e.g. Yu et al., (2007) Science 318:5858); Takahashi et al., (2007) Cell 131(5):861). The various methods and other embodiments described herein may require or utilize hPS cells from a variety of sources. For example, hPS cells suitable for use may be obtained from developing embryos. Additionally or alternatively, suitable hPS cells may be obtained from established cell lines and/or human induced pluripotent stem (hiPS) cells.

As used herein "hiPS cells" refers to human induced pluripotent stem cells.

As used herein, the terms "scaffold" and "tissue scaffold" refer to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, "support scaffold" refers to a larger, macroscopic system to mechanically position and anchor a tissue scaffold.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used herein, a "graft" refers to a cell, tissue or organ that is implanted into an individual or structure, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the terms "tissue grafting" and "tissue reconstructing" both refer to implanting a graft into an individual to treat or alleviate a tissue defect, such as a lung defect or a soft tissue defect.

As used herein, to "alleviate" a disease, defect, disorder or condition means reducing the severity of one or more symptoms of the disease, defect, disorder or condition.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

As used herein, the term "growth medium" is meant to refer to a culture medium that promotes growth of cells. A growth medium will generally contain animal serum. In some instances, the growth medium may not contain animal serum. In some instances a growth medium will promote cell proliferation.

"Differentiation medium" is used herein to refer to a cell growth medium comprising an additive or a lack of an additive such that a stem cell, fetal pulmonary cell or other such progenitor cell, that is not fully differentiated, develops into a cell with some or all of the characteristics of a differentiated cell when incubated in the medium.

As used herein, the term "growth factor" refers to a protein, peptide, mitogen, or other molecule having a growth, proliferative, differentiative, or trophic effect on a cell. Growth factors include, but are not limited to, fibroblast growth factor (FGF), basic fibroblast growth factor (bFGF), acidic fibroblast growth factor (aFGF), epidermal growth factor (EGF), insulin-like growth factor-I (IGF-T), insulin-like growth factor-II (IGF-II), platelet-derived growth factor (PDGF), vascular endothelial cell growth factor (VEGF), activin-A, bone morphogenic proteins (BMPs), insulin, growth hormone, erythropoietin, thrombopoietin, interleukin 3 (IL-3), interleukin 6 (IL-6), interleukin 7 (IL-7), macrophage colony stimulating factor, c-kit ligand/stem cell factor, osteoprotegerin ligand, insulin, nerve growth factor, ciliary neurotrophic factor, cytokines, chemokines, morphogens, neutralizing antibodies, other proteins, and small molecules. Preferably, the FGF is selected from the group selected from FGF2, FGF7, FGF10, and any combination thereof.

An "isolated cell" refers to a cell which has been separated from other components and/or cells which naturally accompany the isolated cell in a tissue or mammal.

As used herein, a "fetal pulmonary cells" (FPCs) refer to cells isolated from the lung tissue of an embryo. A mixed population of FPCs can include, but is not limited to epithelial, mesenchymal, and endothelial cells.

As used herein, "epithelial cell" means a cell which forms the outer surface of the body and lines organs, cavities and mucosal surfaces.

As used herein, "endothelial cell" means a cell which lines the blood and lymphatic vessels and various other body cavities.

As used herein, a "substantially purified" cell is a cell that is essentially free of other cell types. Thus, a substantially purified cell refers to a cell which has been purified from other cell types with which it is normally associated in its naturally-occurring state.

"Expandability" is used herein to refer to the capacity of a cell to proliferate, for example, to expand in number or, in the case of a population of cells, to undergo population doublings.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein "endogenous" refers to any material from or produced inside an organism, cell or system.

"Exogenous" refers to any material introduced into or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally-occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

The term "tissue," as used herein includes, but is not limited to, bone, neural tissue, fibrous connective tissue including tendons and ligaments, cartilage, dura, pericardia, muscle, lung, heart valves, veins and arteries and other vasculature, dermis, adipose tissue, or glandular tissue.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein, the term "vasculature" includes any part of the circulatory system in a tissue, organ, or body part of a subject.

As used herein, the term "negative pressure" is used with respect to negative pressure perfusion and/or negative pressure ventilation. In negative pressure perfusion/ventilation, fluid or air is brought into the organ because the pressure around the organ is lowered in relation to that of the interior of the organ. Fluid or air is expelled from the organ because the pressure around the organ is raised relative to that of inside the organ.

As used herein, the term "positive pressure" is used with respect to positive pressure perfusion and/or positive pressure ventilation. In positive pressure perfusion/ventilation, fluid or air is pushed into the organ because the pressure in the fluid lines is increased relative to the pressure within the fluid compartments of the organ. Fluid or air is pulled from the organ because pressure in the fluid lines is lowered relative to pressure within the fluid compartments of the organ.

As used herein, the term "hydraulic" relates to objects or actions operated by, or involving, an incompressible fluid moving in a confined space under pressure. In one embodiment of the present invention, negative pressure ventilation and perfusion are brought about by hydraulic action.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides a bioreactor system for the culture of large-mammal pulmonary tissue. Preferably, the pulmonary tissue is a lung tissue. In one embodiment, the pulmonary tissue is an intact lung. In one embodiment, the bioreactor system supports at least one of the decellularization, recellularization, and culture of an engineered lung. In one embodiment, the engineered lung is a human lung. In one embodiment, the bioreactor is designed to provide either positive or negative pressure perfusion and ventilation. The bioreactor of the invention allows for the sterile ventilation and perfusion of the engineered lung at a wide range of physiological parameters. In one embodiment, function of the bioreactor is highly controllable and regulatable, providing substantially greater control over fluid flow than previous designs. In one embodiment, the bioreactor system of the invention comprises a support scaffold that provides support of the large weight of large-mammal lung constructs. In another embodiment, the bioreactor system comprises a pleural sack which surrounds the engineered lung, thereby providing a small-volume sterile reservoir encompassing the engineered lung, which reduces the amount of culture media needed to support the lung.

The present invention is partly based upon the unique design of a hydraulic driven system, wherein hydraulically mediated changes in the volume of fluid filled bioreactor chambers induces negative pressure ventilation and/or perfusion. The hydraulic drive negative pressure ventilation/perfusion employed by one embodiment of the invention is made possible because each fluid compartment of the bioreactor is manufactured with non-compliant or rigid walls, and is filled fully with incompressible fluid. In this way, changes in the volume of each fluid compartment induce a specific volume of fluid to enter and leave the lung tissue through various pathways. The hydraulic driven bioreactor system of the present invention is a highly controlled and monitored design.

In one embodiment, the bioreactor system of the present invention is capable of anterograde, retrograde, circulatory and oscillatory flow, with any fluid, through either airways or vasculature. Further, in one embodiment, the bioreactor system of the present invention is capable of both negative pressure and positive pressure perfusion as well as both negative pressure and positive pressure ventilation. Thus, the bioreactor of the present invention is highly flexible in the modes and patterns of fluid delivery to the engineered tissue. For example, in one embodiment, the bioreactor of present invention allows for the delivery of fluid to both sides of the vasculature at once and then be pushed out via negative-pressure contraction of the organ.

The present invention also provides an engineered large-mammal pulmonary tissue cultured in the bioreactor of the invention. In one embodiment, the engineered pulmonary tissue exhibits branching morphogenesis exemplified by natural pulmonary tissue. Thus, the invention provides an in vitro model that mimics natural pulmonary tissue. The in vitro three dimensional pulmonary tissue model is useful for among other things, drug discovery, toxicity testing, disease pathology, and the like.

In some instances, the engineered three dimensional pulmonary tissue comprises cells cultured on the tissue. Any suitable cells can be used for culturing on the decellularized tissue of the invention. Suitable cells include but are not limited to human iPS cells, human iPS-derived endothelium, human iPS-derived respiratory epithelium, human iPS-derived endoderm, and the like. In some instances, the iPS cells are cultured on the decellularized tissue for regeneration of lung tissue. In some instances, iPS cells are cultured on the decellularized tissue.

After seeding, the cells on the scaffold are optionally subjected to an expansion medium or to a differentiation medium or cultured in the presence of tissue-specific growth factors. The composition is then implanted into a subject in need thereof. The subject may be a mammal, but is preferably a human and the source of the cells for growth and implantation is any mammal, preferably a human. The implanted composition supports additional cell growth in vivo, thus providing tissue reconstruction. Accordingly, the invention provides the use of engineered three dimensional pulmonary tissue for tissue grafting therapies.

The invention also includes generation of pulmonary tissue in vivo. Preferably, vascularized pulmonary tissue is generated in vivo. In one aspect, the fetal pulmonary cells are administered in the context of the decellularized tissue to a mammal to facilitate in vivo pulmonary tissue formation.

In the present invention, it is demonstrated that the bioreactor system of the invention is capable of producing a vascularized three dimensional pulmonary tissue model for preclinical in vitro pharmacological, physiological, and scientific testing. In addition, the pulmonary tissue can be seeded with suitable cells, such as neonatal pulmonary cells or autologous pulmonary cells, and the resultant composition can be used for tissue reconstruction in vivo.

The compositions and methods of the instant invention have myriad useful applications. The compositions may be used in therapeutic methods for alleviating or treating tissue defects in an individual. The compositions may also be used in vitro or in vivo to identify therapeutic compounds and therefore may have therapeutic potential.

Bioreactor—Overview

The invention provides a system (e.g., a bioreactor) for culturing lung tissue. The bioreactor enables the maintenance of cell viability, cellular differentiation state, and lung morphology. In one embodiment, decellularized scaffolds, when cultured in the bioreactor with a suitable cell source, can support the adherence and proliferation of a wide range of cell types, including pulmonary endothelial, epithelial, and mesenchymal cells. In one embodiment, the bioreactor is constructed to provide structural support and integrity to a large-mammal engineered lung. In another embodiment, the bioreactor comprises a pleural sack, which surrounds the engineered lung, thereby reducing the amount of media required for culture. In one embodiment, the bioreactor comprises a two-part hydraulic chamber that allows for the sterile manipulation of the attached lung tissue.

The bioreactor of the invention incorporates key features of the in vivo environment. The bioreactor is designed to allow modifications for optimizing and customizing decellularization and/or recellularization processes. In one embodiment, the bioreactor is capable of perfusing media through the vasculature of the engineered lung tissue at a rate specified by the user and preferably within the physiological flow and pressure levels of a mammal. In one embodiment, the bioreactor is capable of positive-pressure and negative-pressure perfusion. In another embodiment, the bioreactor is capable of ventilating the tissue (e.g., lung) with air or media through the trachea. Preferably, negative pressure ventilation is used in order to be consistent with normal physiological conditions, though ventilation using positive pressure can also be done. In yet another embodiment, the bioreactor is capable of allowing different media types to bathe the vascular and airway compartments of the tissue. In another embodiment, the bioreactor allows for gas exchange into the culture medium, while simultaneously meeting the desired requirements for ventilation. In another embodiment, the bioreactor has ports to allow for pressure measurements, for example measurements of the pulmonary artery and tracheal pressures. Preferably, pressures are within normal physiological values. In another embodiment, the bioreactor has a means of allowing media exchange on a periodic basis.

The bioreactor of the invention generally includes at least one cannulation device for cannulating a tissue, at least one circuit for supplying fluid through the cannula(s), and means (e.g., a chamber) to maintain a sterile environment for the organ or tissue. A cannulation device generally includes size-appropriate hollow tubing for introducing into a vessel, duct, and/or cavity of a tissue. Typically, one or more vessels, ducts, and/or cavities are cannulated in a tissue. A fluid circuit can include a reservoir for the fluid (e.g., a cellular disruption medium) and a mechanism for moving the fluid through the organ (e.g., hydraulic action, pump, air pressure, gravity) via the one or more cannulae. The sterility of a tissue during decellularization, recellularization, and/or culture can be maintained using the methods discussed elsewhere herein.

In one embodiment, the bioreactor is used to decellularize and recellularize tissues as described herein. The process can be monitored for certain perfusion characteristics (e.g., pressure, volume, flow pattern, temperature, gases, pH), mechanical forces (e.g., ventricular wall motion and stress), and electrical stimulation (e.g., pacing). The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the bioreactor and/or the tissue. Sonomicrometry, micromanometry, and/or conductance measurements can be used to acquire pressure-volume. For example, sensors can be used to monitor the pressure of a liquid moving through a cannulated organ or tissue; the ambient temperature in the system and/or the temperature of the organ or tissue; the pH and/or the rate of flow of a liquid moving through the cannulated organ or tissue; and/or the biological activity of a recellularizing tissue. In addition to having sensors for monitoring such features, a system for decellularizing and/or recellularizing a tissue also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, an external pacemaker, and/or a compliance chamber. To help ensure stable conditions (e.g., temperature), the chambers, reservoirs and tubings can be water-jacketed.

The bioreactor is capable of providing sufficient nutrient supply and mechanical stimulation to the lung tissue in order to support cell survival and differentiation. The bioreactor can be used for in vitro lung tissue culture and for engineered lung tissue culture. Preferably, the bioreactor is used to culture engineered lung tissue using decellularized lung scaffolds.

The development of a bioreactor capable of the in vitro culture of true 3-dimensional segments of lung tissue is an important step in the development of clinically useful engineered lung tissue. For example, growth and maturation of the engineered lung tissue can take place in the bioreactor prior to implantation of the engineered lung into a recipient, thereby enhancing the functionality of the final implanted lung tissue in vivo. In addition, the bioreactor for in vitro lung culture can be used to assist the study of pulmonary biology, physiology, and development. That is, the interactions of lung endothelial and epithelial cells to form the alveolar-capillary barrier can be studied using the engineered lung tissue and bioreactor of the invention. A skilled artisan would be able to study lung behavior in a more controlled environment than the various animal models currently used. The engineered lung tissue and bioreactor could also be used for pharmacologic testing and investigation in human or animal tissue before proceeding to time-consuming and costly human or animal trials.

Bioreactor—Detailed

The present invention provides a bioreactor system designed to culture an engineered lung for long time spans under mechanical and chemical conditioning. In some instances, the bioreactor system is referred to as the reactor. In one embodiment, the engineered lung is a decellularized lung of a large-mammal, including, for example, a human. In one embodiment, the engineered lung is seeded with cells. The reactor is capable of breathing the organ in a sterile fashion, at a wide range of physiologic rates, and allows for a high degree of breathing control and calibration. In one embodiment, the engineered lung is ventilated via positive pressure ventilation. In another embodiment, the engineered lung is ventilated via negative pressure ventilation. The reactor is also capable of vascular perfusion of the organ at a wide range of physiologic rates, also in a highly controlled, self-contained, sterile fashion. In one embodiment, all components of the reactor designed to be in media contact are autoclavable and made from biocompatible materials. For example, in one embodiment, the components of the reactor are made from USP class VI materials. In one embodiment, the reactor contains scaffolding for positioning and orienting the engineered lung within a sealed chamber. In another embodiment, the reactor comprises a system for cannulating and mounting the engineered lung within this scaffold. In one embodiment, the reactor comprises an artificial pleura that drastically reduces the fluid volume required for organ culture, maintains the organ's shape, position and orientation, and acts as a sterile barrier that allows for the disassembly and maintenance of the reactor outside of a hood without sterile compromise. The reactor is designed to be easy to use and highly flexible, allowing for the variation of a number of parameters and the easy integration of standard sensing equipment and monitoring technology. Various set-ups allows for the real-time measurement of gas and nutrient levels, pH, pressure, and flow rates of each fluid reservoir.

The bioreactor of the present invention was designed and constructed with the goal of decellularization, reseeding, and growth of an engineered human or large-mammal lung construct. The design criteria of an exemplary bioreactor are as follow:

i. Provide a sterile environment for the construct during all stages of decellularization and culture.

ii. Allow for the easy cannulation and mounting of the engineered lung within the reactor, as well as easy observation of the surgical cannulations while the lung is mounted in the reactor.

iii. Provide a way to reliably position and orient the lung within the reactor iv. Allow for the disassembly and bench-top maintenance of the reactor outside of a sterile environment, without compromising the sterility of the lung itself v. Reduce the media volume required for whole-lung culture. This is an important criteria, as large volumes (10-30 liters) of cell-specific media cost tens of thousands of dollars a week in an application such as this.

vi. Provide a method to negative-pressure breath the organ (while still allowing for positive-pressure breathing if necessary) at rates and volumes highly similar to those experienced by the organ in vivo, allowing for variable breath volume, pressure, and rate. This must be done in a fashion that in no way compromises sterility.

vii. Provide a method to perfuse fluid through the vasculature of the organ in a pulsatile fashion highly similar to that experienced by the organ in vivo, allowing for variable stroke volume, pressure, and rate. This must be done in a fashion that in no way compromises sterility.

viii. Allow for easy integration of third-party monitoring/sensory equipment or technology ix. Design a system that is easy to use, compact, self-contained, and readily mobile for transport between workstations.

In some instances, the bioreactor of the present invention satisfies some, most, or all of these criteria, thereby providing an efficient bioreactor system for the culture of a large-mammal engineered lung.

As depicted in FIG. 1, an exemplary bioreactor system 100 of the invention generally comprises an organ chamber 10, a hydraulic drive 30, a vascular circuit 40, and a tracheal circuit 60. In some embodiments, organ chamber 10 provides a sterile housing for the engineered lung 11. In some embodiments, organ chamber 10 is completely filled with fluid. Hydraulic drive 30 pumps fluid in and out of hydraulic reservoir 12 to change the fluid volume of organ chamber 10 and thereby moving fluid in and out of lung 11. Vascular circuit 40 provides fluid through arterial line 41 to the artery of lung 11, while also collecting fluid from the vein of lung 11, via venous line 42. Tracheal circuit 60 provides fluid through inhalation line 61 to the trachea/bronchi of lung 11, while also collecting fluid from lung 11 via exhalation line 62. In one embodiment, tracheal circuit 60 further comprises a pleural drain line 63.

Figure 2:
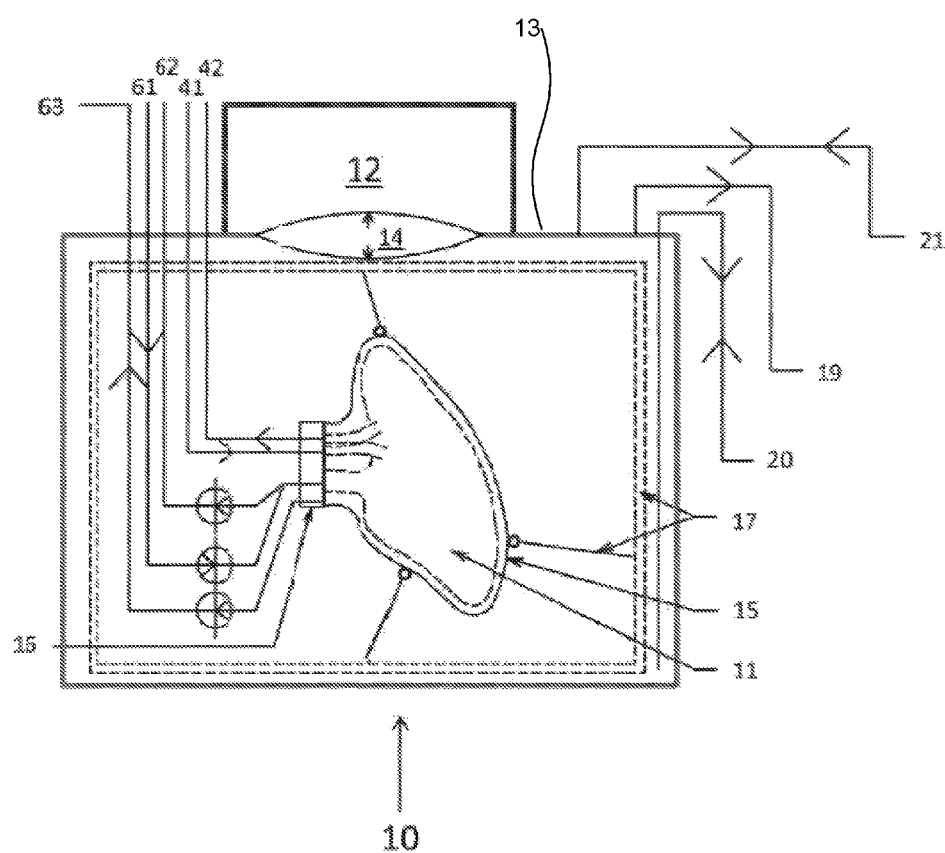
FIG. 2 is a schematic for an exemplary chamber of one embodiment of the bioreactor of the invention.
Figure 6:
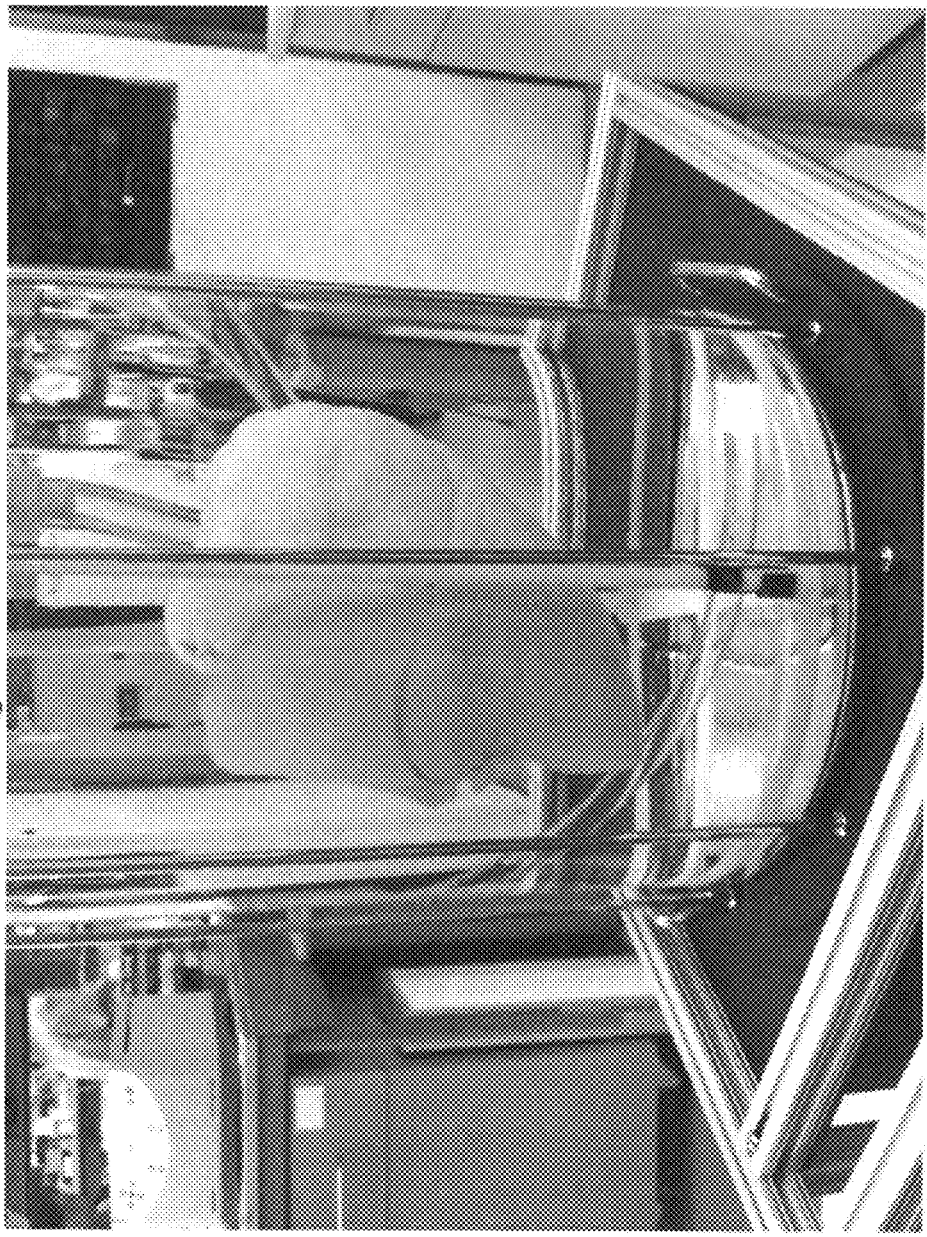
FIG. 6 is an image depicting an exemplary chamber and engineered lung of one embodiment of the bioreactor of the invention.

FIG. 2 is an isolated view of organ chamber 10, which houses engineered lung 11. FIG. 6 is an image depicting an exemplary chamber 10 comprising lung 11. As contemplated herein, chamber 10 may be any suitable size and/or shape that accommodates a lung of a large mammal (e.g. a human). In one embodiment, chamber 10 is sized and shaped to accommodate a pair of large-mammal lungs. In one embodiment, chamber 10 is manufactured from any rigid material, including, for example, plastic, glass, and the like. In some embodiments, chamber 10 is at least partially filled with fluid. In one embodiment, chamber 10 is completely filled with fluid. A fluid filled chamber 10 allows the volume changes of hydraulic chamber 12 to be directly reflected, via a fixed 1:1 ratio, in the expansion and contraction of lung 11. In one embodiment, chamber 10 is partially or completely filled with culture media. In another embodiment, chamber 10 is partially or completely filled with any suitable fluid, while lung 11 is bathed in culture media housed in pleural sack 15, as described elsewhere herein. For example, in one embodiment, chamber 10 is filled with water, saline, and the like. As discussed elsewhere herein, in certain embodiments, inclusion of pleural sack 15 allows for the use of a relatively smaller amount of media, and thus chamber 10 can be filled with an inexpensive fluid (e.g. water). In one embodiment, chamber 10 is constructed to withstand pressures of up to 10 psi. In another embodiment, chamber 10 is constructed to withstand pressures of up to 100 psi. While not required, in some embodiments, chamber 10 is constructed of a material that is optically clear. In one embodiment, chamber 10 is sealed such that its contents remain sterile. In one embodiment, chamber 10 is easily and reversibly assembled and disassembled to allow for access to interior components as well as to lung 11 and pleural sack 15.

Chamber 10 comprises a top plate 13, which may include hydraulic reservoir 12 and/or isolation diaphragm 14. In one embodiment, top plate 13 comprises several fluid ports that allows for fluid flow into and out of chamber 10. The fluid ports may be of any type known in the art. For example, in one embodiment, the fluid ports are ½ inch NPT female ports, allowing the attachment and incorporation of a wide variety of equipment. In one embodiment, the fluid ports comprise quick-disconnect tubing fittings, which allows for sterile disconnect of tubing from top plate 13. Hydraulic reservoir 12 is in fluid communication with hydraulic drive 30, which pumps fluid into and out of hydraulic reservoir 12. The pumping of fluid into and out of hydraulic reservoir 12 alters the volume of hydraulic reservoir 12. In one embodiment, isolation diaphragm 14 is a compliant membrane that separates hydraulic reservoir 12 from the rest of chamber 10. Isolation diaphragm 14 forms at least one wall of hydraulic reservoir 12 and allows the volume change of hydraulic reservoir 12 to directly change the volume of chamber 10, thereby allowing negative pressure ventilation and perfusion of lung 11. This hydraulic-driven method allows for the amount of fluid into and out of lung 11 to be precisely known and controlled. Isolation diaphragm 14 may be composed of any suitable compliant material known in the art. For example, in one embodiment, isolation diaphragm 14 is a silicone membrane. Isolation diaphragm 14 isolates the fluid in chamber 10 from the fluid in hydraulic reservoir 12, thereby allowing sterile negative pressure ventilation and perfusion. In embodiments where the entire chamber 10 is filled with culture media, isolation diaphragm 14 provides a sterile barrier between the media and fluid of hydraulic reservoir 12. In one embodiment, top plate 13 further comprises a sealing ring beneath isolation diaphragm 14 that allows for sterile fluid flow without disruption of the membrane barrier between the fluid of chamber 10 and of hydraulic chamber 12.

Figure 7:
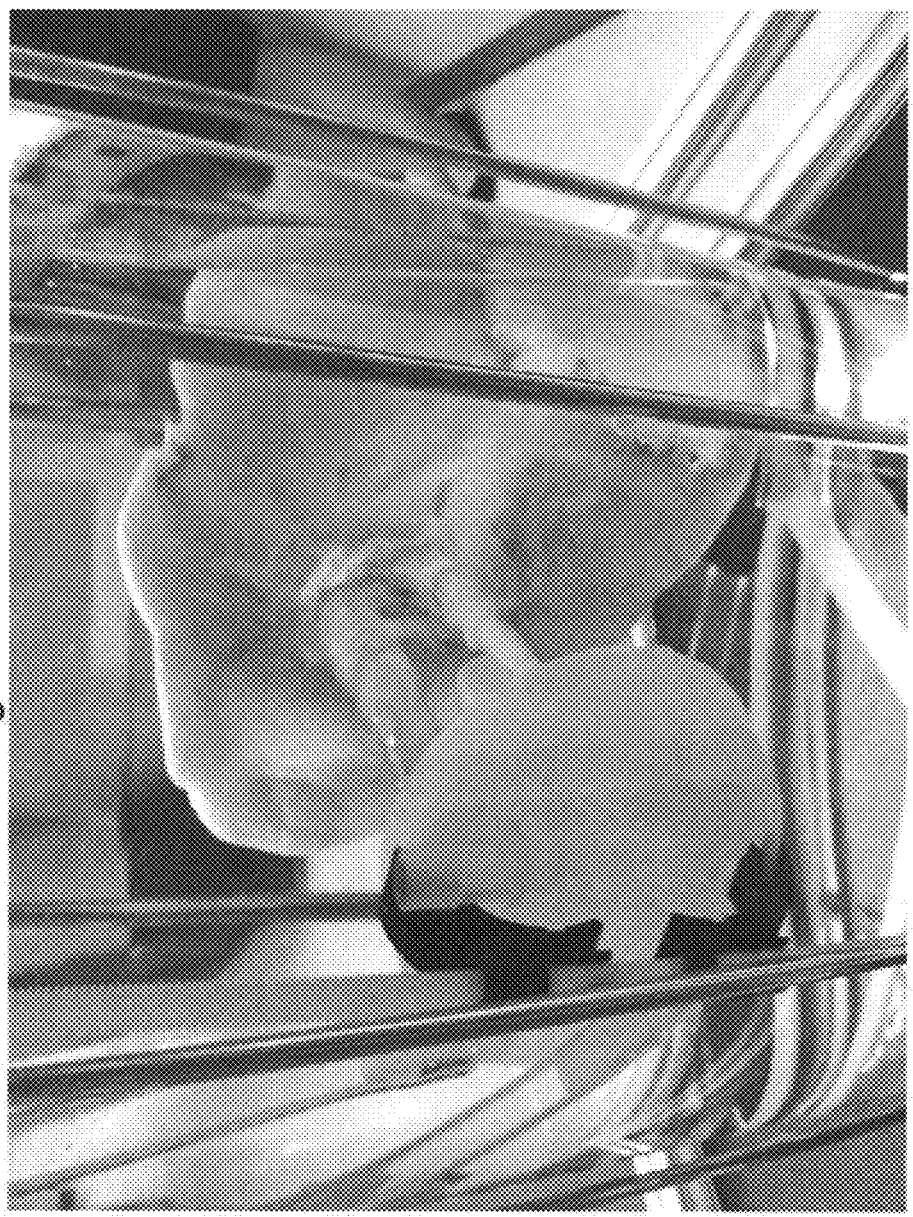
FIG. 7 is an image depicting the connection of a lung with an exemplary cannulation port.
Figure 8:
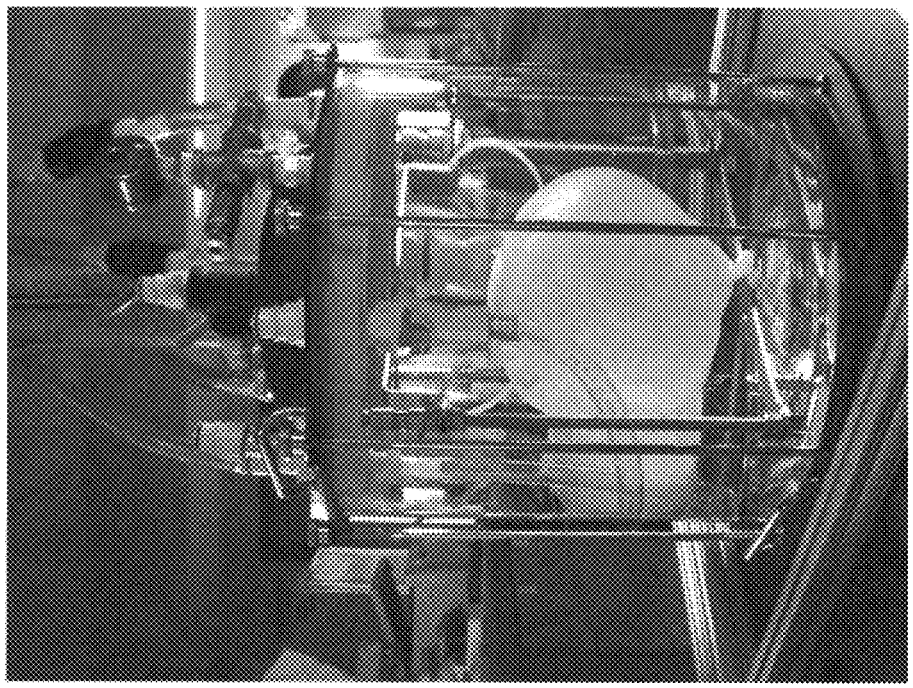
FIG. 8 is an image depicting an exemplary chamber and pleural sack of one embodiment of the bioreactor of the invention.

As depicted in FIG. 2, organ chamber 10 may also comprise a sterile pleural sack 15, a cannulation port 16, a support scaffold 17, and anchor points 18. Pleural sack 15 is a shaped structure that provides a sterile barrier surrounding lung 11, thereby providing an isolated fluid reservoir between lung 11 and pleural sack 15. FIG. 8 depicts one embodiment of the invention where chamber 10 comprises pleural sack 15. Thus, in one embodiment, pleural sack 15 isolates culture media within pleural sack 15 from the fluid of chamber 10. Any type of suitable culture media may be used within pleural sack 15. Non-limiting examples of suitable culture media include Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with nonessential amino acids), and the like. The presence of pleural sack 15 drastically reduces the amount of culture media required for efficient culture of lung 11. In one embodiment, pleural sack 15 is shaped in a way to hold lung 11 in a physiological orientation and configuration during decellularization, ventilation, and perfusion. Pleural sack 15 may be constructed of any suitable, biocompatible elastic material. For example, in one embodiment, pleural sack 15 is constructed of highly-elastic silicone. Thus, pleural sack 15 is designed and constructed to readily expand and contract during ventilation of lung 11. Cannulation port 16 attaches to lung 11 such that the cannulations of lung 11 are attached to one side of cannulation port 16, while the other side of cannulation port 16 is connected to tubing lines running to top plate 13 (FIG. 7). For example, in one embodiment, cannulation port 16 is attached to arterial line 41, venous line 42, inhalation line 61, exhalation line 62, pleural drain line 63, or combinations thereof. In one embodiment, cannulation port 16 also functions as a sealing ring for pleural sack 15, thereby helping to form the isolated media chamber between lung 11 and pleural sack 15. Cannulation port 16 is constructed of any suitable material known in the art, including, for example, plastic, glass, silicone, and the like. Together, pleural sack 15 and cannulation port 16 allow for sterile disconnection, storage, and transportation of lung 11 outside of chamber 10.

Inclusion of pleural sack 15 and cannulation port 16 in bioreactor system 100 provides a unique mechanism to reduce infections and costs associated with tissue engineered culture. Together, pleural sack 15 and cannulation port 16 provides a sterile barrier around lung 11, independent of chamber 10. Fluid is still able to flow into and out of lung 11, without contacting the surrounding fluid within chamber 10. This significantly reduces the risk of infection, while allowing easy handling, mounting, and manipulation of lung 11 outside of a sterile hood. Further, pleural sack 15 and cannulation port 16 form a small isolated media chamber surrounding lung 11, which significantly reduces the media volume required for culture, while still allowing for lung 11 to expand and contract in physiological function. Pleural sack 15 and cannulation port 16 also provides an anchor point for the attachment of support scaffold 17. This allows for proper positioning of lung 11 within chamber 10. As described elsewhere herein, support scaffold 17, along with pleural sack 15 and cannulation port 16 provide the necessary support to stabilize the weight of lung 11, which may be particularly important when chamber 10 is not filled with fluid.

Support scaffold 17 provides a rigid scaffold with chamber 10 that allows for the positioning and orientation of lung 11 within chamber 10. The lung of a large-mammal can be quite heavy, and thus support scaffold 17 aids in supporting lung 11 within chamber 10. A consequence of scaling up tissue engineering to human-sized organs is that the constructs are massively heavier and more awkward than small-mammal models. Thus, bioreactor systems using small-mammal organs do not require interior scaffolding, because these tissues are strong enough to support their own weight (or buoyancy) via cannulation alone. However, it has been presently discovered that when working with large-mammal (e.g. human) organs, incorporating a scaffold into the bioreactor system is necessary. In one embodiment, support scaffold 17 of the present invention serves to position and orient lung 11. In one embodiment, support scaffold 17 supports lung 11 when not suspended in fluid. In one embodiment, support scaffold 17 anchors lung 11 when ventilated with air. In one embodiment support scaffold 17 is constructed of any suitable rigid material known in the art, including, but not limited to plastic and glass. In one embodiment, support scaffold 17 is constructed of a biocompatible material. Support scaffold 17 is connected to pleural sack 15 via anchor points 18. The number of anchor points 18 will vary depending on the structural needs of lung 11. In one embodiment, support scaffold 17 is also connected to cannulation port 16. Support scaffold 17 allows for set up and transfer of lung 11, pleural sack 15, and cannulation port 16 to and from chamber 10. Further, in one embodiment, support scaffold 17 is reversibly removed from chamber 10, with lung 11 and pleural sack 15 still mounted, without compromising sterility, thereby acting as a free-standing support for the attached lung 11. In this way, support scaffold 17 allows for easy and sterile adjustments of line connections and lung 11 position. Thus, in one embodiment, support scaffold 17 acts as a stand for benchtop maintenance during periods of culture. Together, the linking of support scaffold 17 with pleural sack 15 allows for supporting the weight of lung 11, even when chamber 10 is not filed with fluid, or when the chamber 10 is disassembled.

In one embodiment, chamber 10 further comprises a pressure relief system 19. In one embodiment, pressure relief system 19 comprises at least one pressure relief valves. For example, in one embodiment, pressure relief system 19 comprises two pressure relief valves. In another embodiment, pressure relief system 19 comprises a pressure monitor and/or a pressure sensor. As would be understood by one skilled in the art, any pressure monitor known in the art that allows continuous or periodic measurement of pressure with chamber 10 is suitable for use in the present invention. One exemplary pressure monitor that can be used in conjunction with pressure relief system 19 is PendoTECH Pressure MAT Monitor/Transmitter (PendoTech, Princeton, N.J.). The at least one pressure relief valve ensures that the pressure within chamber 10 does not go above a programmed maximum pressure or below a programmed minimum pressure. Pressure relief system 19 therefore prevents damage to chamber 10 and bioreactor system 100 should a fluidic line become blocked or otherwise malfunction.

In one embodiment, chamber 10 further comprises at least one fill/drain line 20. In one embodiment, chamber 10 comprises two fill/drain lines 20. For example, in one embodiment, chamber 10 comprises one fill/drain line 20 terminating at the top of chamber 10 and another fill/drain line 20 terminating at the bottom of chamber 10. Fill/drain line 20 allows for chamber 10 to be quickly filled and drained, while remaining sterilely sealed.

In one embodiment, chamber 10 further comprises a thermal regulation system 21, which maintains the temperature of the fluid in chamber 10. In one embodiment, thermal regulation system 21 obviates the need for placing chamber 10 within an incubator, thereby allowing for benchtop operation of bioreactor system 100. This is critical in that, in some embodiments, chamber 10 is too large to fit into conventional incubators. In one embodiment, thermal regulation system 21 comprises a heat source, for example, an immersion heating coil. In another embodiment, thermal regulation system 21 comprises a temperature sensor which continuously or periodically provides a measurement of the temperature within chamber 10. In one embodiment, thermal regulation system 21 ensures that the temperature within chamber 10 does not go above a programmed maximum temperature or below a programmed minimum temperature.

Figure 3:
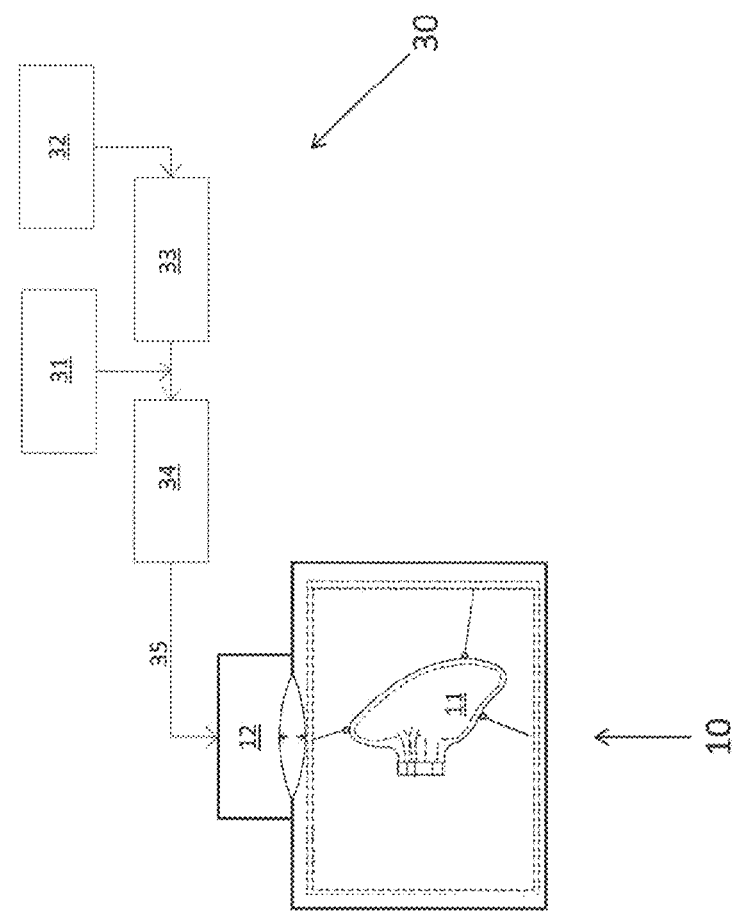
FIG. 3 is a schematic for an exemplary hydraulic drive of one embodiment of the bioreactor of the invention.
Figure 9:
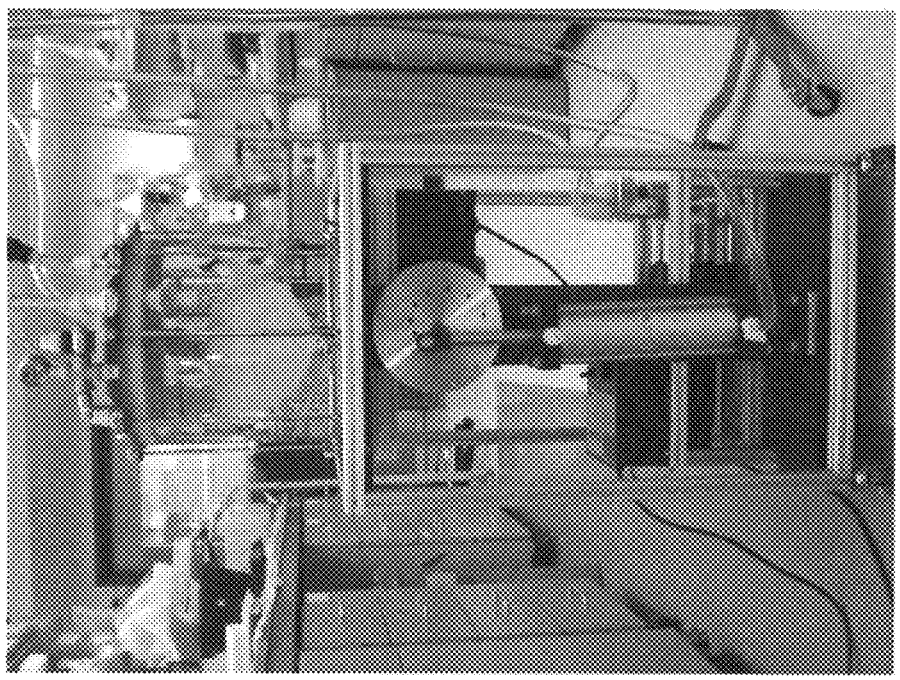
FIG. 9 is an image depicting an exemplary chamber, hydraulic drive, and vascular drive of one embodiment of the invention.

FIG. 3 is an isolated view of hydraulic drive 30 connected to chamber 10. Hydraulic drive 30 may generally include a volume controller 31, cycle rate controller 32, drive motor 33, hydraulic breathing volume pump 34, and hydraulic line 35. In one embodiment, drive motor 33 comprises a gear motor. In one embodiment, cycle rate controller 32 comprises a variable-speed drive. In one embodiment, volume controller 31 comprises a variable offset drive-arm. In one embodiment, hydraulic breathing volume pump comprises a hydraulic piston. Pumping fluid into and out of hydraulic reservoir 12, via hydraulic line 35, causes the expansion and contraction of hydraulic reservoir 12, as allowed by the compliance of isolation diaphragm 14. Expansion and contraction of hydraulic reservoir 12 alters the volume of chamber 10, which subsequently drives the expansion and contraction of pleural sack 15 and lung 11. In this way, hydraulic drive 30 provides negative-pressure perfusion and/or ventilation, as further described elsewhere herein. Hydraulic line 35 provides fluid communication between hydraulic breathing volume pump 34 to hydraulic reservoir 12. In one embodiment, hydraulic line 35 consists of standard tubing, as would be understood by those skilled in the art. As would be understood by those skilled in the art, hydraulic drive 30 may include any additional components that allows for pumping of fluid into and out of hydraulic reservoir 12. In one embodiment, hydraulic drive 30 is capable of ventilation between 0-15 cycles per minute. In a preferred embodiment, hydraulic drive 30 is capable of ventilation between 0-30 cycles per minute. In one embodiment, hydraulic drive 30 produces a stroke volume of about 10-1000 mL. In a preferred embodiment, hydraulic drive 30 produces a stroke volume of about 20-750 mL. An exemplary hydraulic drive 30 is depicted in FIG. 9.

Figure 4:
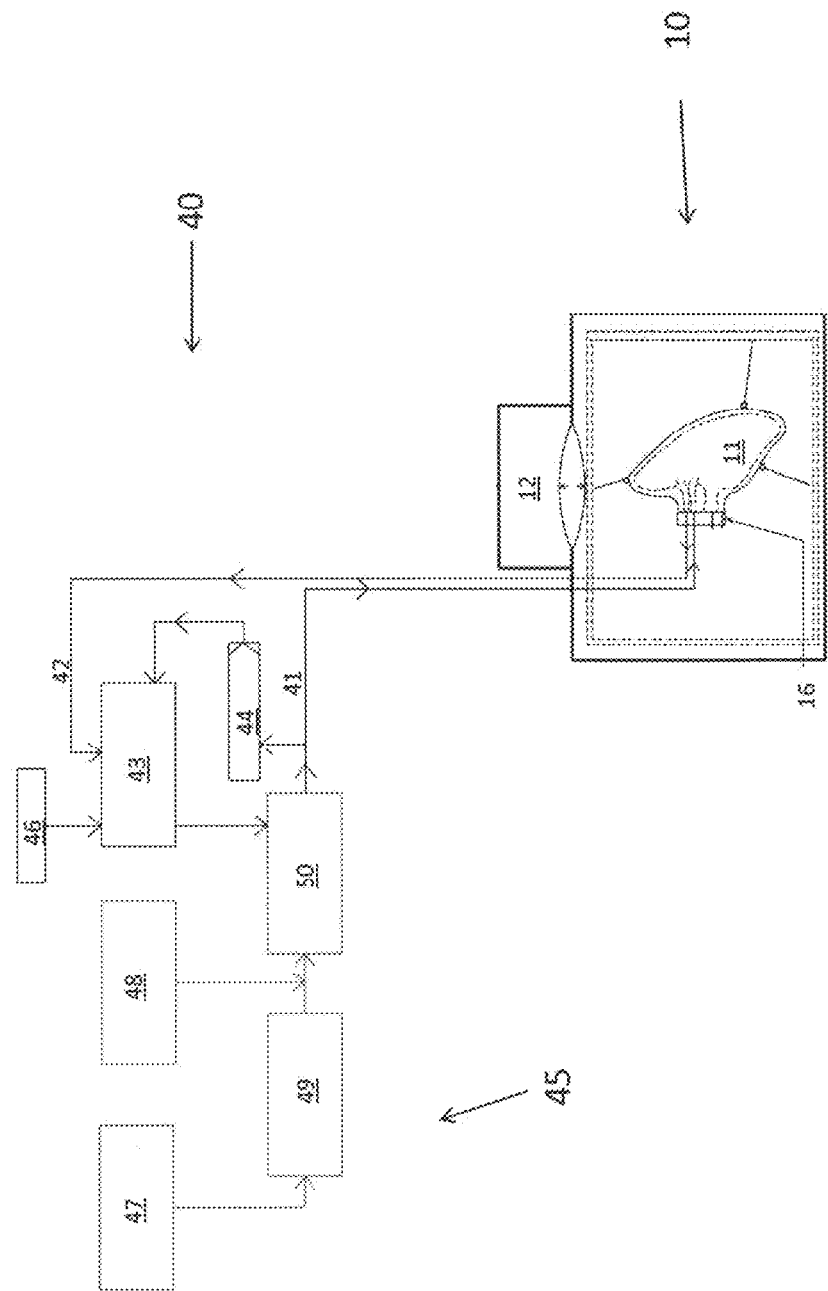
FIG. 4 is a schematic for an exemplary vascular drive and vascular circuit of one embodiment of the bioreactor of the invention.
Figure 10:
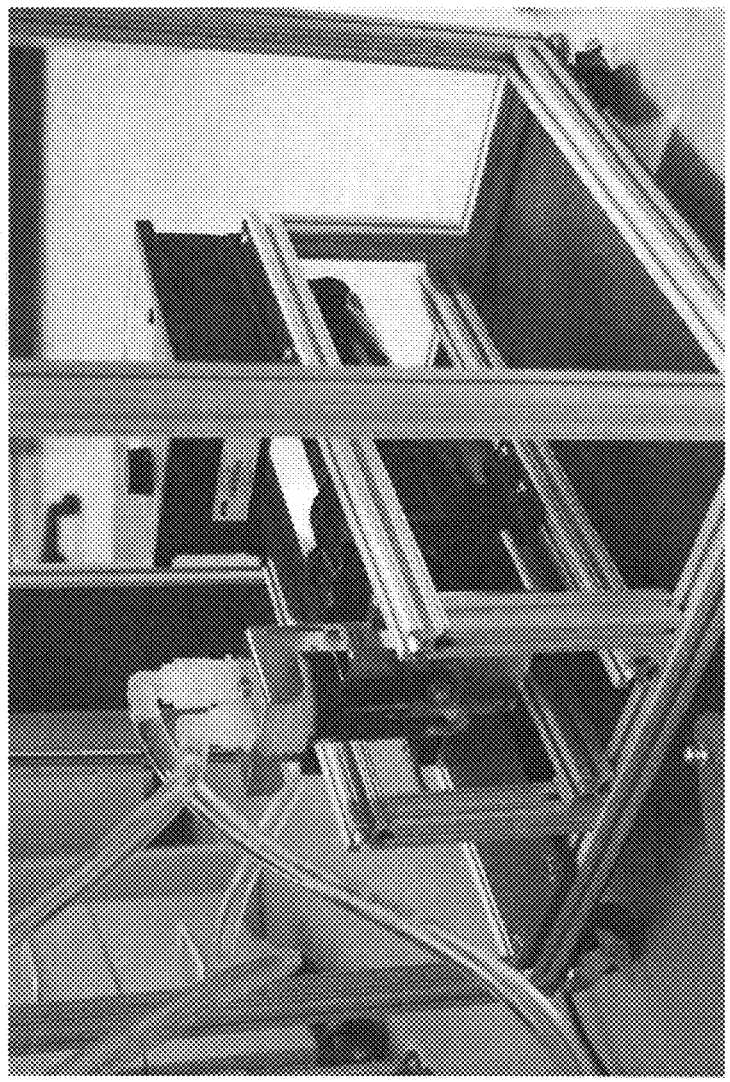
FIG. 10 is an image depicting an exemplary vascular drive of one embodiment of the invention.

FIG. 4 is an isolated view of vascular circuit 40, which comprises arterial line 41, venous line 42, vascular fluid reservoir 43, adjustable systolic pressure relief valve 44, vascular drive 45, and vascular reservoir gas exchange mechanism 46. In one embodiment, vascular drive 45 is a bellows drive. In some embodiments, vascular drive 45 comprises a cycle rate controller 47, a volume controller 48, a drive motor 49, and a hydraulic vascular volume pump 50. In one embodiment, drive motor 49 comprises a gear motor. In one embodiment, cycle rate controller 47 comprises a variable-speed drive. In one embodiment, volume controller 48 comprises a variable-off set drive arm. In one embodiment, hydraulic vascular volume pump 50 comprises a cyclically compliant chamber. In one embodiment hydraulic vascular volume pump 50 comprises a bellows pump, with physiological "duckbill" valves. Vascular drive 45 pumps vascular fluid, via arterial line 41, to the artery of lung 11. As would be understood by those skilled in the art, vascular drive 45 may include any additional components that allows for pumping of vascular fluid to the artery of lung 11. In one embodiment, vascular drive 45 is capable of producing pulse rates between 0-50 cycles per minute. In a preferred embodiment, vascular drive 45 is capable of producing pulse rates between 0-94 cycles per minute. In one embodiment, vascular drive 45 produces a stroke volume of about 0-100 mL. In a preferred embodiment, vascular drive 45 produces a stroke volume of about 0-55 mL. An exemplary vascular drive 45 is depicted in FIG. 10.

In certain embodiments, vascular reservoir 43 comprises vascular fluid for delivery to the vasculature of lung 11. In one embodiment, vascular fluid is a liquid. In one embodiment, the vascular fluid is a decellularization solution. In another embodiment, vascular fluid is a recellularization solution, where the solution comprises a cell and is delivered to lung 11 during recellularization of a lung scaffold. In another embodiment, the vascular fluid comprises culture media. In another embodiment, the vascular fluid comprises plasma, serum, and/or blood. In another embodiment, the vascular fluid comprises water, saline, or the like. Vascular circuit 40 provides vascular fluid to the vasculature of lung 11. Arterial line 41 carries vascular fluid from vascular reservoir 43 to the artery of lung 11, while venous line 42 carries vascular fluid from the vein of lung 11 to vascular reservoir 43. In certain embodiments, arterial line 41 and venous line 42 comprise any type of standard tubing capable of fluid delivery.

In one embodiment, vascular circuit 40 provides volume metered pulsatile perfusion to lung 11. In this mode of perfusion, vascular drive 45 pumps vascular fluid throughout the circuit. The volume metered pulsatile perfusion carried out by vascular circuit 40 in the present invention provides significantly greater degree of control, precision, and accuracy over perfusion stroke volume, rate, and characteristics than in previous systems.

In another embodiment, vascular circuit 40 provides pressure metered pulsatile perfusion to lung 11. In this mode, adjustable systolic pressure relief valve 44 allows for vascular flow to be pressure metered while using the same circuitry components. In one embodiment, adjustable systolic pressure relief valve 44 is set to limit systolic pressure. In this embodiment, when the pressure in arterial line 41 is higher than this set value, flow of vascular fluid is diverted back to vascular reservoir 43, thereby bypassing delivery to lung 11. In this pressure metered pulsatile perfusion mode, the height of vascular fluid within vascular reservoir 43 determines the diastolic pressure. In one embodiment, vascular reservoir 43 itself is at atmospheric pressure at all times. For example, in one embodiment, vascular reservoir 43 is vented to the outside environment. In another embodiment, vascular reservoir 43 is constructed of a compliant material. In the pressure metered pulsatile perfusion mode, the pulse rate is still determined by the settings of vascular drive 45, but the stroke volume is dependent on the pressure. This pressure metered pulsatile perfusion mode is a capability not present in prior bioreactor systems.

In another embodiment, vascular circuit 40 and hydraulic drive 30 work together to provide hydraulic-driven negative-pressure perfusion in bioreactor system 100. In this hydraulic-driven negative-pressure perfusion mode, hydraulic drive 30 pumps fluid in to and out of hydraulic reservoir 12, thereby creating pressure changes within hydraulic reservoir 12 and chamber 10. In embodiments where chamber 10 is completely filled with fluid, the walls of chamber 10 are rigid, and other cannulae are capped, vascular fluid consequently flows to and from the lungs from vascular reservoir 43. In one embodiment, the induced negative-pressure promotes pulsatile circulatory flow, where vascular fluid enters the arterial side of the lung vasculature and exits via the venous side. In another embodiment, the induced negative-pressure generates oscillatory, non-circulating flow, where vascular fluid that enters one side of the vascular tree exits via the same cannulations, without being forced through the capillary bed. Hydraulically driven negative-pressure perfusion has the capacity to be more finely-tuned and calibrated than positive-pressure perfusion. This capability is particularly useful for certain portions of lung decellularization, cell seeding, and culture.

Figure 5:
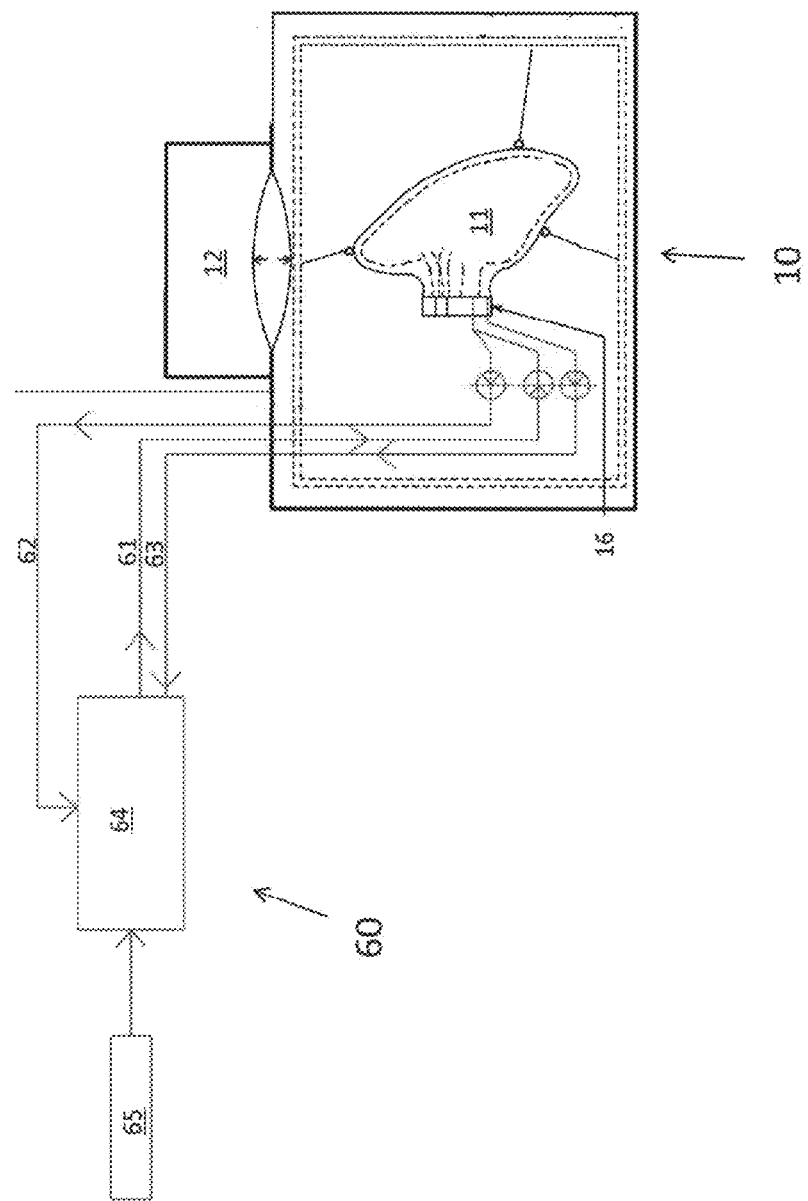
FIG. 5 is a schematic for an exemplary tracheal circuit of one embodiment of the bioreactor of the invention.

As depicted in FIG. 5, tracheal circuit 60 comprises inhalation line 61, exhalation line 62, pleural drain line 63, tracheal reservoir 64, and tracheal reservoir gas exchange mechanism 65. Tracheal circuit 60 provides tracheal fluid to the airways of lung 11. Inhalation line 61 carries tracheal fluid from tracheal reservoir 64 and the airways of lung 11, while exhalation line 62 carries tracheal fluid from the airways of lung 11 to tracheal 64. Pleural drain line 63 connects tracheal reservoir 64 with the isolated reservoir within pleural sack 15, allowing the drainage of fluid that may have seeped into the space between lung 11 and pleural sack 15. As contemplated herein, inhalation line 61, exhalation line 62, and pleural drain line 63 may be constructed from any type of standard tubing capable of fluid delivery.

In certain embodiments, tracheal reservoir 64 comprises tracheal fluid for delivery to the airway of lung 11. In one embodiment, tracheal fluid is a liquid. In another embodiment, tracheal fluid is a gas. For example, in one embodiment tracheal fluid is air. In one embodiment, the tracheal fluid is a decellularization solution. In another embodiment, tracheal fluid is a recellularization solution, where the solution comprises a cell and is delivered to lung 11 during recellularization of a lung scaffold. In another embodiment, the tracheal fluid comprises culture media. In another embodiment, the tracheal fluid comprises plasma, serum, and/or blood. In another embodiment, the tracheal fluid comprises water, saline, or the like. In one embodiment tracheal reservoir 64 itself is at atmospheric pressure at all times. For example, in one embodiment, tracheal reservoir 64 is vented to the outside environment. In another embodiment, tracheal reservoir 64 is constructed of a compliant material.

In one embodiment, tracheal circuit 60 and hydraulic drive 30 work together to provide hydraulic-driven negative-pressure ventilation in bioreactor system 100. In this hydraulic-driven negative-pressure ventilation mode, hydraulic drive 30 pumps fluid in to and out of hydraulic reservoir 12, thereby creating volume changes within hydraulic reservoir 12 and chamber 10. In embodiments where chamber 10 is completely filled with fluid, and the walls of chamber 10 are rigid, tracheal fluid consequently flows to and from the lungs from tracheal reservoir 64. In one embodiment, the induced negative-pressure promotes pulsatile circulatory flow, where tracheal fluid enters the airway through inhalation line 61 and exits through exhalation line 62. In another embodiment, the induced negative-pressure generates oscillatory, non-circulating flow, where tracheal fluid that enters and exits the airway of lung 11 through the same cannulations. Hydraulically driven negative-pressure ventilation provides a far greater degree of control, precision and accuracy over breathing volume, rate, and mechanics than other bioreactor systems.

In certain embodiments, bioreactor system 100 is capable of simultaneous negative-pressure ventilation and negative-pressure perfusion. In some embodiments, inhalation line 61 and exhalation line 62 of tracheal circuit 60 are sealed, thereby allowing only negative-pressure perfusion from vascular circuit 40. In another embodiment, arterial line 41 and venous line 42 of vascular circuit 40 are sealed thereby allowing only negative-pressure ventilation from tracheal circuit 60. In other embodiments, negative-pressure ventilation is combined with pressure-driven or volume-metered perfusion.

In one embodiment, vascular reservoir 43 and/or tracheal reservoir 65 are gas regulated during culture within bioreactor system 100. In one embodiment, vascular circuit 40 comprises vascular reservoir gas exchange mechanism 46. In one embodiment, tracheal circuit 60 comprises tracheal reservoir gas exchange mechanism 65. As would be understood by those skilled in the art, vascular reservoir gas exchange mechanism 46 and/or tracheal reservoir gas exchange mechanism 65 may include any known mechanism that regulates gas exchange in vascular reservoir 43 and/or tracheal reservoir 64. In certain embodiments, vascular reservoir gas exchange mechanism 46 and/or tracheal reservoir gas exchange mechanism 65 comprise a commercially available bioprocess gas regulation system. In one embodiment, the walls of vascular reservoir 43 and/or tracheal reservoir 64 are constructed from a highly-gas permeable material. In another embodiment, vascular reservoir 43 and/or tracheal reservoir 64 are placed in an incubator. In one embodiment, vascular reservoir gas exchange mechanism 46 and tracheal reservoir gas exchange mechanism 65 comprise sterile filters that allow adequate gas exchange in the reservoirs.

In certain embodiments, the reservoirs of bioreactor system 100 must be thermally controlled during culture. As described above, in one embodiment, chamber 10 comprises temperature regulation system 21 that measures and controls the temperature within chamber 10. In another embodiment, chamber 10 is surrounded by a water jacket, thereby insulating chamber 10. In certain embodiments, water jacketing of chamber 10 allows for benchtop operation. In another embodiment, chamber 10, vascular reservoir 43, and/or tracheal reservoir 64 are placed in a temperature controlled incubator. In another embodiment, chamber 10, vascular reservoir 43, and/or tracheal reservoir 64 are placed in a temperature controlled water bath.

In certain embodiments, bioreactor system 100 weighs over 100 pounds. Thus, in one embodiment, the components of bioreactor system 100 are associated with a wheeled cart that can support the weight of the complete system. In one embodiment, one or more components are integrated into the cart. In another embodiment, one or more components are separately portable, but are positioned within the cart.

Decellularization

In some embodiments, the bioreactor system of the invention supports the decllularization of a large-mammal lung. In one embodiment, the present invention provides a method of making engineered tissue scaffolds using a decellularized tissue as a starting source, preferably a decellularized natural tissue derived from a large mammal (e.g. human).

As would be understood by those skilled in the art, any process of decellularization may be used in conjunction with the bioreactor of the invention. For example, U.S. Patent Application Publication No. US2012/0064050 describes an exemplary decellularization method used for the decellularization of pulmonary tissue, the disclosure of which is incorporated herein by reference in its entirety.

In one embodiment, the decellularization process relies on a chemical methodology. In one aspect, the chemical solution or otherwise referred to as the decellularization solution used for decellularization generally includes at least a hypertonic solution, a detergent, and a chelating agent. Preferably, the hypertonic solution is a hypertonic sodium chloride solution. Preferably, the detergent is a zwitterionic detergent such as CHAPS. Preferably, the chelating agent is EDTA.

In one embodiment, the decellularization solution can include a buffer (e.g., PBS) for osmotic compatibility with the cells. In some instances, the decellularization solution also can include enzymes such as, without limitation, one or more collagenases, one or more dispases, one or more DNases, or a protease such as trypsin. In some instances, the decellularization solution also or alternatively can include inhibitors of one or more enzymes (e.g., protease inhibitors, nuclease inhibitors, and/or collegenase inhibitors).

In one embodiment, the method to decellularize a tissue of the invention includes perfusing the tissue with the decellularization solution. The pressure for which the decellularization solution is perfused through the tissue can be adjusted to the desired pressure. Preferably, the decellularization solution is perfused through the tissue at perfusion pressure below about 30 mmHg. More preferably, the decellularization solution is perfused through the tissue at pressures less than about 20 mmHg. In one embodiment, the decellularization solution is perfused through the tissue at pressures between 9 and 18 mmHg.

In one embodiment, the decellularization solution can be introduced into the airway of the lung tissue to effect cell removal. The bioreactor of the invention facilitations a number of different modes and patterns of fluid flow, discussed elsewhere herein, which can be utilized for the delivery of decellularization solution.

In one embodiment, the decellularized tissue of the invention consists essentially of the extracellular matrix (ECM) component of all or most regions of the tissue, including ECM components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Successful decellularization is defined as the absence of detectable myofilaments, endothelial cells, smooth muscle cells, epithelial cells, and nuclei in histologic sections using standard histological staining procedures. Preferably, but not necessarily, residual cell debris also has been removed from the decellularized tissue.

In one embodiment, the decellularization process of a natural tissue preserves the native 3-dimensional structure of the tissue. That is, the morphology and the architecture of the tissue, including ECM components are maintained during and following the process of decellularization. The morphology and architecture of the ECM can be examined visually and/or histologically. For example, the basal lamina on the exterior surface of a solid organ or within the vasculature of an organ or tissue should not be removed or significantly damaged due to decellularization. In addition, the fibrils of the ECM should be similar to or significantly unchanged from that of an organ or tissue that has not been decellularized.

In one embodiment, one or more compounds can be applied in or on a decellularized tissue to, for example, preserve the decellularized tissue, or to prepare the decellularized tissue for recellularization and/or to assist or stimulate cells during the recellularization process. Such compounds include, but are not limited to, one or more growth factors (e.g., VEGF, DKK-1, FGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized organ or tissue can be further treated with, for example, irradiation (e.g., UV, gamma) to reduce or eliminate the presence of any type of microorganism remaining on or in a decellularized tissue.

Use of the decellularization solution of the invention to generate a decellularized tissue provides a controlled, precise way to destroy cells of a tissue, while leaving the underlying ECM, including vascularization, and other gross morphological features of the original tissue intact. The decellularized scaffolds are then suitable for seeding with appropriate cells. Where the process is performed in vitro, the seeded tissue is suitable for implantation into the recipient as a replacement tissue. In addition to the decellularized tissues themselves, the invention includes methods of fabrication of engineered tissues built from such scaffolds.

The present invention provides a method suitable for producing a tissue scaffold for use in tissue engineering. Although the source of the tissue is not limited, in exemplary embodiments, the tissue is from a relatively large animal or an animal recognized as having a similar anatomy (with regard to the tissue of interest) as a human, such as a pig, a cow, a horse, a monkey, or an ape. In some embodiments, the source of the tissue is human, use of which can reduce the possibility of rejection of engineered tissues based on the scaffold. In preferred embodiments, the method leaves intact vascular structures of the tissue, as well as alveolar architecture with preservation of the alveolar septae. As used herein, the term "intact" refers to a state of being whereby an element is capable of performing its original function to a substantial extent.

In one embodiment, the decellularized lung retains several key characteristics of normal lung matrix. For example, the decellularized lung comprises at least one or more of collagen, elastin, fibronectin, and proteoglycan.

The decellularized tissue does not retain either major histocompatibility complex (MHC) class I or II antigen, therefore the tissue does not elicit an adverse an immune response when administered to a recipient.

The decellularized tissue retains mechanics properties of normal native lung. The decellularized tissue also retains some of the barrier function of normal native lung.

Compositions

Compositions of the invention include an engineered large-mammal lung tissue. Preferably, the engineered lung tissue exhibits any one or more of the following properties: 1) vasculature and airway, where there is a patent, perfused vasculature and a patent airway tree that can be ventilated; 2) gas exchange, where the engineered lung is capable of exchanging sufficient gas between the airway and vascular compartments to support the physiological needs of the recipient; most preferably, the partial pressure of oxygen in the pulmonary vein is at least 50 mmHg; 3) mechanics, where the engineered tissue is strong enough to withstand all needed movements, in particular breathing motions and vascular perfusion, as well as manipulation during surgical implantation; 4) immunogenicity, where the engineered lung tissue does not provoke an immune response when implanted into the recipient.

The compositions and methods of the instant invention can be practiced using any suitable cell. Preferably, the suitable cell or cells are regenerative and can be used to recellularize the decellularized tissue of the invention. An example of a regenerative cells includes, but is not limited to, a stem cell, an embryonic stem cell, an adult stem cell, an umbilical cord blood cell, an inducible pluripotent stem cell (iPSC), a tissue-derived stem or progenitor cells, bone marrow-derived step or progenitor cells, blood-derived stem or progenitor cell, a mesenchymal stem cells (MSC), a skeletal muscle-derived cells, a multipotent adult progentitor cell (MAPC), a fetal pulmonary cell, differentiated pulmonary epithelial cells, pulmonary progenitor cells, vascular progenitor cells, differentiated vascular cells and the like. Additional regenerative cells that can be used include bone marrow-derived stem cells such as bone marrow mononuclear cells (BM-MNC), endothelial or vascular stem or progenitor cells, and peripheral blood-derived stem cells such as endothelial progenitor cells (EPC).

Preferably, the suitable cell is isolated from a mammal, more preferably a primate and more preferably still, a human. The cells useful in the methods of the present invention are isolated using methods known in the art. Following isolation, the suitable cells are cultured in a culture medium.

As a non-limiting example, inducible pluripotent stem cell (iPSCs) are described in more detailed with respect to culturing the cells. However, a skilled artisan will recognize that the culturing conditions can be modified to the suitable cell. Media formulations that support the growth of iPSCs include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with nonessential amino acids), and the like.

The invention also provides cells that "seed" the scaffold. In this context, the decellularized organ or tissue is contacted with a population of cells, either differentiated (mature or primary) cells, stem cells (e.g., iPS cells), or partially differentiated cells. Thus, the cells can be totipotent cells, pluripotent cells, or multipotent cells, and can be uncommitted or committed, and may be single-lineage cells. The cells may be undifferentiated cells, partially differentiated cells, or fully differentiated cells including fetal derived cells.

The number of cells that is introduced into and onto a decellularized organ in order to generate an organ or tissue is dependent on both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be seeded with at least about 1,000 (e.g., at least 10,000, 100,000, 1,000, 000, 10,000,000, or 100,000,000) regenerative cells; or can have from about 1,000 cells/mg tissue (wet weight, i.e., prior to decellularization) to about 10,000,000 cells/mg tissue (wet weight) attached thereto.

Cells can be introduced to a decellularized organ or tissue by injection into one or more locations. In addition, more than one type of cell (i.e., a cocktail of cells) can be introduced into a decellularized organ or tissue. For example, a cocktail of cells can be injected at multiple positions in a decellularized organ or tissue or different cell types can be injected into different portions of a decellularized organ or tissue. Alternatively, or in addition to injection, regenerative cells or a cocktail of cells can be introduced by perfusion into a cannulated decellularized organ or tissue. For example, cells can be perfused into a decellularized organ using a perfusion medium, which can then be changed to an expansion and/or differentiation medium to induce growth and/or differentiation of the regenerative cells. In the case of a lung tissue, the cells can be introduced into either or both of the airway compartment via the trachea, or the vascular compartment via the pulmonary artery or vein. In one embodiment of the bioreactor of the present invention, cells are introduced into the engineered lung by adding a cell suspension to the vascular reservoir and/or tracheal reservoir.

During recellularization, an organ or tissue is maintained under conditions in which at least some of the regenerative cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or tissue and the cells attached thereto are maintained in a suitable environment. For example, the cells may require a nutritional supplement (e.g., nutrients and/or a carbon source such as glucose), exogenous hormones or growth factors, and/or a particular pH.

Cells can be allogeneic to a decellularized organ or tissue (e.g., a human decellularized organ or tissue seeded with human cells), or regenerative cells can be xenogeneic to a decellularized organ or tissue (e.g., a pig decellularized organ or tissue seeded with human cells).

In some instances, an organ or tissue generated by the methods described herein is to be transplanted into a patient. In those cases, the cells used to recellularize a decellularized organ or tissue can be obtained from the patient such that the regenerative cells are autologous to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue can be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

In certain instances, a decellularized tissue may be recellularized with cells in vivo (e.g., after the tissue has been transplanted into an individual). In vivo recellularization may be performed as described above (e.g., injection and/or perfusion) with, for example, any of the cells described herein. Alternatively or additionally, in vivo seeding of a decellularized organ or tissue with endogenous cells may occur naturally or be mediated by factors delivered to the recellularized tissue.

Administration

The invention contemplates use of the engineered large-mammal tissues in both in vitro and in vivo settings. Thus, the invention provides for use of the engineered tissues for research purposes and for therapeutic or medical/veterinary purposes. In research settings, an enormous number of practical applications exist for the technology. One example of such applications is use of the engineered tissues in an ex vivo cancer model, such as one to test the effectiveness of various ablation techniques (including, for example, radiation treatment, chemotherapy treatment, or a combination) in a lab, thus avoiding use of ill patients to optimize a treatment method. For example, one can attach a recently removed lung to a bioreactor and treat the lung to ablate tissue. Another example of an in vivo use is for tissue engineering.

The engineered tissues of the present invention have use in vivo. Among the various uses, mention can be made of methods of in vivo treatment of subjects (used interchangeably herein with "patients", and meant to encompass both human and animals). In general for certain embodiments, methods of treating subjects comprise implanting an engineered tissue according to the invention into or on the surface of a subject, where implanting of the tissue results in a detectable change in the subject. The detectable change can be any change that can be detected using the natural senses or using man-made devices. While any type of treatment is envisioned by the present invention (e.g., therapeutic treatment of a disease or disorder, cosmetic treatment of skin blemishes, etc.), in many embodiments, the treatment is a therapeutic treatment of a disease, disorder, or other affliction of a subject. As such, a detectable change may be detection of a change, preferably an improvement, in at least one clinical symptom of a disease or disorder affecting the subject. Exemplary in vivo therapeutic methods include regeneration of organs after treatment for a tumor, preparation of a surgical site for implantation of a medical device, skin grafting, and replacement of part or all of a tissue or organ, such as one damaged or destroyed by a disease or disorder. Exemplary organs or tissues include: heart, lung, liver, kidney, urinary bladder, brain, ear, eye, or skin. In view of the fact that a subject may be a human or animal, the present invention has both medical and veterinary applications.

In one embodiment, the method comprises exposing a tissue to the decellularization methods of the invention to kill cells of the treated tissue and to create a tissue scaffold. The method can further comprise seeding the tissue scaffold with cells, and allowing the seeded cells to proliferate in and on the tissue scaffold. Proliferation produces a regenerated tissue that contains healthy and functional cells.

The invention also provides methods of treating a patient by implanting an engineered lung tissue into a mammal in need thereof. In some instances, the engineered lung tissue comprises suitable cells, for example iPS cells. However, the invention should not be limited to any particular type of cells. After implantation, the grafted cells can respond to environmental cues that will cause it to develop characteristics of the endogenous tissue. Preferably, the cells form histiotypic alveolar-like structures, comprised of differentiated distal epithelial cells (proSpC expressing) forming ductal structures. Thus, the implanted cells will develop characteristics that liken it to the surrounding tissue. Using these methods, the biological scaffolding can augment the tissue; the biological scaffolding of the invention can be used for tissue engineering and in any conventional tissue engineering setting.

Accordingly, the invention encompasses tissue regeneration applications. The objective of the tissue regeneration therapy approach is to deliver high densities of repair-competent cells (or cells that can become competent when influenced by the local environment) to the defect site in a format that optimizes both initial wound mechanics and eventual neotissue production. The composition of the instant invention is particularly useful in methods to alleviate or treat lung tissue defects in individuals. Advantageously, the composition of the invention provides for improved lung tissue regeneration. Specifically, the tissue regeneration is achieved more rapidly as a result of the inventive composition.

Advantageously, the compositions and methods of the invention represent an improvement over prior art methods. In one embodiment, the composition for use in treating a lung tissue defect comprises stem cells, preferably iPS cells seeded on a scaffold and cultured in vitro to generate a 3-dimensional culture, as described elsewhere herein.

Model for Drug Discovery

The present invention provides an in vitro method suitable to allow evaluation of test compounds for therapeutic activity with respect to a pulmonary disease or disorder. Preferably, the method includes the use of an engineered three dimensional lung tissue.

The invention is based on the development of a bioreactor for the culture of large-mammal lung tissue. In some instances, the lung tissue is produced from a decellularized lung scaffold, which can be seeded with suitable cells. In some instances, mixed populations of iPS cells which contain epithelial, mesenchymal, and endothelial cells are used to generate the three dimensional engineered lung tissue. For example, the iPS cells are placed within a three dimensional decellularized lung tissue. Thus, the model incorporates the influence of iPS cells on the growth and cell-cell communication with neighboring cells. The three dimensional lung tissue mimics a natural lung tissue, for example the engineered lung tissue exhibits branching morphogenesis exemplified by natural lung tissue. Therefore, in certain embodiments, the engineered lung tissue, grown in the bioreactor of the invention, serves as a model for evaluating the properties of various compositions.

The model is useful for testing drugs on the pathology of a lung tissue. In addition, the model can be used to examine the effects of particular delivery vehicles for therapeutic agents on the pathology of lung tissue, for example, to compare the effects of the same agent administered via different delivery systems, or simply to assess whether a delivery vehicle itself (e.g. a viral vector) is capable of affecting lung pathology.

In one embodiment, the invention provides an in vitro method for screening a test agent for the ability of the test agent to modulate the health of a lung tissue. The method comprises contacting a test agent to an engineered three dimensional lung tissue model and measuring the effect that the test agent has on the lung tissue model. Any alteration to the model in the presence of the test agent is an indication that the test agent is able to modulate the health of a lung tissue.

In another embodiment, the present invention provides an in vitro method for observing an effect a test agent has on a lung tissue, comprising the steps of:

a) providing at least one three-dimensional lung tissue model, wherein the model is intended to model normal lung tissue;

b) contacting the test agent with the lung tissue model; and c) observing the effect the test agent has the lung tissue model.

The tissue model is a construct which comprises a three-dimensional array of cells on a scaffold, for example a collagen matrix, and at least one test cell. The method comprises observing the effect of the test agent on the pathology of the lung tissue. However the method may further comprise the step of observing the effect of the test agent on individual cell types of the lung tissue.

The test agent may be any agent including chemical agents (such as toxins), pharmaceuticals, peptides, proteins (such as antibodies, cytokines, enzymes, etc.), and nucleic acids, including gene medicines and introduced genes, which may encode therapeutic agents such as proteins, antisense agents (i.e. nucleic acids comprising a sequence complementary to a target RNA expressed in a target cell type, such as RNAi or siRNA), ribozymes, etc. Additionally or alternatively, the test agent may be a physical agent such as radiation (e.g. ionizing radiation, UV-light or heat); these can be tested alone or in combination with chemical and other agents.

The model may also be used to test delivery vehicles. These may be of any form, from conventional pharmaceutical formulations, to gene delivery vehicles. For example, the model may be used to compare the effects on a therapeutic effect of the same agent administered by two or more different delivery systems (e.g. a depot formulation and a controlled release formulation). It may also be used to investigate whether a particular vehicle-could have effects of itself on the lung tissue. As the use of gene-based therapeutics increases, the safety issues associated with the various possible delivery systems become increasingly important. Thus the models of the present invention may be used to investigate the properties of delivery systems for nucleic acid therapeutics, such as naked DNA or RNA, viral vectors (e.g. retroviral or adenoviral vectors), liposomes, etc. Thus the test agent may be a delivery vehicle of any appropriate type with or without any associated therapeutic agent.

The test agent may be added to the model to be tested using any suitable means. For example, the test agent may be added drop-wise onto the surface of the model and allowed to diffuse into or otherwise enter the model, or it can be added to the nutrient medium and allowed to be perfused through the organ. The model is also suitable for testing the effects of physical agents such as ionizing radiation, UV-light or heat alone or in combination with chemical agents (for example, in photodynamic therapy).

Observing the effect the test agent has on the model can be accomplished using a variety of methods. For example, a particular agent may induce a cell to enter apoptosis. Detectable changes in the cell may comprise changes in cell area, volume, shape, morphology, marker expression (e.g. cell surface marker expression) or other suitable characteristic, such as chromosomal fragmentation. Cell number may also be monitored in order to observe the effects of a test agent on cell proliferation; this may be analyzed directly, e.g. by counting the number of a particular cell type present, or indirectly, e.g. by measuring the size of a particular cell mass. These may be observed directly or indirectly on the intact model using, for example, suitable fluorescent cell staining. This can be by pre-labeling of cells with vital dyes or genetically introduced fluorescent markers (for example green fluorescent proteins) for serial analysis of the living model or by fixation and post-labeling with fluorescent substances such as propidium iodide or fluorescently labeled antibodies. Alternatively, models may be processed by normal histological methods, such as immunohistochemistry, using antibodies directed against a suitable cellular target, or in situ hybridization, to test for expression of a particular mRNA species. Moreover, this may be carried out in an automated/robotic or semi-automated manner, using computer systems and software to image the cells at various time points and detect any change in, for example, cell density, location and/or morphology. Confocal laser scanning microscopy in particular permits three-dimensional analysis of intact models. Thus it is possible to apply directly to the intact, three-dimensional lung tissue model, quantitative analysis of cell behavior which are normally only possible for cells in conventional two-dimensional culture. By this means quantitative, serial analysis of cell proliferation, apoptosis, necrosis, migration and matrix invasion, among others, are obtained in a three-dimensional lung tissue model which bridges the gap between conventional two-dimensional cell cultures and live animal models.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Bioreactor

The bioreactor of the present invention was designed and constructed with the goal of decellularization, reseeding, and growth of an engineered human or large-mammal lung construct. The design criteria of an exemplary bioreactor are as follow:

Provide a sterile environment for the construct during all stages of decellularization and culture.

Allow for the easy cannulation and mounting of the engineered lung within the reactor, as well as easy observation of the surgical cannulations while the lung is mounted in the reactor.

Provide a way to reliably position and orient the lung within the reactor

Allow for the disassembly and bench-top maintenance of the reactor outside of a sterile environment, without compromising the sterility of the lung itself Reduce the media volume required for whole-lung culture. This is an important criteria, as large volumes (10-30 liters) of cell-specific media cost tens of thousands of dollars a week in an application such as this.

Provide a method to negative-pressure breath the organ (while still allowing for positive-pressure breathing if necessary) at rates and volumes highly similar to those experienced by the organ in vivo, allowing for variable breath volume, pressure, and rate. This must be done in a fashion that in no way compromises sterility.

Provide a method to perfuse fluid through the vasculature of the organ in a pulsatile fashion highly similar to that experienced by the organ in vivo, allowing for variable stroke volume, pressure, and rate. This must be done in a fashion that in no way compromises sterility.

Allow for easy integration of third-party monitoring/sensory equipment or technology.

Design a system that is easy to use, compact, self-contained, and readily mobile for transport between workstations.

A non-limiting example of the bioreactor of the present invention is depicted in FIGS. 1-10.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A bioreactor for large-mammal lung tissue, the bioreactor comprising:
   a sealable rigid chamber having dimensions to accommodate at least one large-mammal lung derived from one or more large mammals selected from the group consisting of: pigs, cows, horses, and primates,
   a sealable elastic pleural sack comprising a cannulation port, the sealable elastic pleural sack configured for:
     mounting within the rigid chamber, and
     defining an isolated sterile fluid chamber surrounding the at least one large-mammal lung,
   a vascular circuit configured to deliver fluid to vasculature of the at least one large-mammal lung,
   a tracheal circuit configured to deliver fluid to airways of the at least one large-mammal lung, and
   a hydraulic drive configured to modulate a pressure of a fluid within the sealable rigid chamber, thereby modulating a volume of the sealable elastic pleural sack and inducing expansion and contraction of the at least one large-mammal lung.

2. The bioreactor of claim 1, wherein the sealable rigid chamber comprises a support scaffold to provide support for the at least one large-mammal lung.

3. The bioreactor of claim 1, wherein the sealable rigid chamber comprises a hydraulic reservoir, separated by an isolation diaphragm from the rest of the chamber.

4. The bioreactor of claim 3, wherein the hydraulic drive is configured to pump fluid into and out of the hydraulic reservoir, thereby causing the expansion and contraction of the at least one large-mammal lung.

5. The bioreactor of claim 1, wherein the bioreactor is configured for hydraulically driven negative-pressure ventilation.

6. The bioreactor of claim 1, wherein the bioreactor is configured for positive-pressure ventilation.

7. The bioreactor of claim 1, wherein the bioreactor is configured for hydraulically driven negative-pressure perfusion.

8. The bioreactor of claim 1, wherein the bioreactor is configured for positive-pressure perfusion.

9. The bioreactor of claim 1, wherein the bioreactor is configured for pulsatile perfusion.

10. The bioreactor of claim 1, wherein the bioreactor is configured for administering anterograde, retrograde, circulatory and oscillatory flow of a fluid to the airways and vasculature of the at least one large-mammal lung.

11. The bioreactor of claim 10, wherein the bioreactor is configured for delivering fluid to the vasculature via both hydraulically driven negative-pressure ventilation and positive-pressure ventilation, and is further configured for delivering fluid to the airways via both hydraulically driven negative-pressure ventilation and positive-pressure ventilation.

12. The bioreactor of claim 1, wherein the bioreactor is configured for the simultaneous delivery of a fluid to an arterial side and a venous side of the lung vasculature followed by the expulsion of the fluid via negative-pressure contraction of the at least one large-mammal lung.

13. The bioreactor of claim 1, wherein the vascular circuit comprises a bellows drive.

14. The bioreactor of claim 1, wherein the vascular circuit is configured to deliver a decellularization solution to the lung to decellularize the at least one large-mammal lung.

15. The bioreactor of claim 1, wherein the tracheal circuit is configured to deliver a decellularization solution to the lung to decellularize the at least one large-mammal lung.

16. The bioreactor of claim 1, wherein the vascular circuit is configured to deliver a solution comprising a cell to the at least one large-mammal lung.

17. The bioreactor of claim 16, wherein the population of cells comprises a stem cell.

18. The bioreactor of claim 1, wherein the tracheal circuit is configured to deliver a solution comprising a cell to the at least one large-mammal lung.

19. The bioreactor of claim 1, wherein the bioreactor is configured for decellularizing the at least one large-mammal lung.

20. The bioreactor of claim 1, wherein the bioreactor is configured for recellularizing the at least one large-mammal lung.

21. The bioreactor of claim 1, wherein the bioreactor is configured for supporting the growth and survival of pulmonary cells.

22. The bioreactor of claim 1, wherein the at least one large-mammal lung is seeded with a population of cells.

23. A bioreactor for large-mammal lung tissue, the bioreactor comprising:
   a sealed rigid chamber comprising an isolation diaphragm, the sealed rigid chamber having dimensions to accommodate at least one large-mammal lung derived from one or more large mammals selected from the group consisting of: pigs, cows, horses, and primates,
   a sealed elastic pleural sack comprising a cannulation port, the sealed elastic pleural sack:
     mounted within the rigid chamber, and
     defining an isolated sterile fluid chamber surrounding the at least one large-mammal lung,
   a vascular circuit configured to deliver fluid to vasculature of the at least one large-mammal lung,
   a tracheal circuit configured to deliver fluid to airways of the at least one large-mammal lung,
   a hydraulic reservoir mounted outside of the sealed rigid chamber over the isolation diaphragm, and
   a hydraulic drive configured to pump fluid into and out of the hydraulic reservoir to modulate a volume of a fluid within the sealable rigid chamber, thereby modulating a volume of the sealed elastic pleural sack and inducing expansion and contraction of the at least one large-mammal lung.

* * * * *